(12) United States Patent
Asahina et al.

(10) Patent No.: US 7,153,851 B2
(45) Date of Patent: Dec. 26, 2006

(54) 10-(3-CYCLOPROPYLAMINOMETHYL-1-PYRROLIDINYL)PYRIDOBENZOXAZINECARBOXYLIC ACID DERIVATIVE EFFECTIVE AGAINST RESISTANT BACTERIUM

(75) Inventors: Yoshikazu Asahina, Tochigi (JP); Masaya Takei, Tochigi (JP)

(73) Assignee: Kyorin Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/508,154

(22) PCT Filed: Mar. 13, 2003

(86) PCT No.: PCT/JP03/02967

§ 371 (c)(1),
(2), (4) Date: Sep. 17, 2004

(87) PCT Pub. No.: WO03/078439

PCT Pub. Date: Sep. 25, 2003

(65) Prior Publication Data

US 2005/0182052 A1    Aug. 18, 2005

(30) Foreign Application Priority Data

Mar. 18, 2002  (JP)  ............................. 2002-074783
Dec. 20, 2002  (JP)  ............................. 2002-369205

(51) Int. Cl.
C07D 498/06  (2006.01)
A61K 31/5383  (2006.01)
A61P 31/04  (2006.01)

(52) U.S. Cl. .................... 514/230.2; 544/101
(58) Field of Classification Search ............... 544/101; 514/230.2
See application file for complete search history.

(56) References Cited

FOREIGN PATENT DOCUMENTS

| EP | 900793 | 3/1999 |
|---|---|---|
| JP | 62-155282 | 7/1987 |
| JP | 10-287669 | 10/1998 |

OTHER PUBLICATIONS

Kawakami et al. (Antimicrobial Agents And Chemotherapy, Aug. 2000, p. 2126-2129).*
Katsuhiro Kawakami, et al., "Antimycobacterial activities of novel levofloxacin analogues", Antimicrobial Agents and Chemotherapy, vol. 44, No. 8, pp. 2126-2129, 2000.

* cited by examiner

Primary Examiner—Kahsay Habte
(74) Attorney, Agent, or Firm—Wenderoth, Lind & Ponack, L.L.P.

(57) ABSTRACT

A compound as represented by the general formula (I) shown below exhibits high antibacterial activity against gram-positive bacteria, in particular, such drug-resistant bacteria as mRNA, PRSP and VRE:

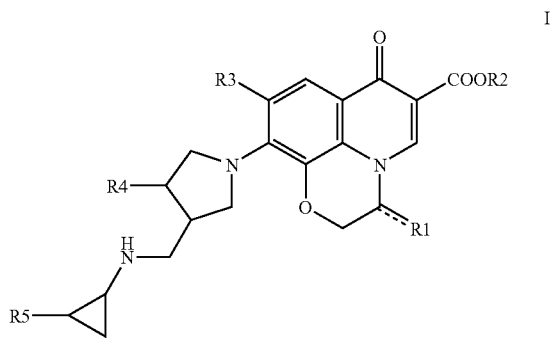

wherein R1 is a methyl group, a fluoromethyl group, a methoxymethyl group, an acetoxymethyl group, a hydroxymethyl group or a methylene; R2 is a hydrogen atom, a lower alkyl group having 1 to 3 carbon atoms, or a pharmaceutically acceptable cation and an ester of a prodrug; R3 is a hydrogen atom or a halogen atom; R4 is a hydrogen atom, a lower alkyl group having 1 to 3 carbon atoms, a fluoromethyl group, a trifluoromethyl group or a fluorine atom; and R5 is a hydrogen atom or a fluorine atom, with exceptions where R1 is a methyl group, R4 and R5 are at the same time a hydrogen atom, and R3 is a fluorine atom.

13 Claims, No Drawings

10-(3-CYCLOPROPYLAMINOMETHYL-1-PYRROLIDINYL)PYRIDOBENZO-XAZINECARBOXYLIC ACID DERIVATIVE EFFECTIVE AGAINST RESISTANT BACTERIUM

TECHNICAL FIELD

The present invention relates to novel 10-(3-cyclopropylaminomethyl-1-pyrrolidinyl)pyridobenzoxazine carboxylic acid derivatives, salts and hydrates thereof that, in addition to being safe and exhibiting strong antibacterial activities, are effective against drug-resistant bacteria that are less susceptible to conventional antibacterial agents.

TECHNICAL BACKGROUND

Reference should be made to the following articles: Japanese Patent Laid-Open Publication No. Sho 57-46986 (Patent Article 1); Japanese Patent Laid-Open Publication No. Sho 61-204188 (Patent Article 2); Japanese Patent Laid-Open Publication No. Sho 62-155282 (Patent Article 3).

Since the development of norfloxacin, considerable effort has been made worldwide to develop quinolone carboxylic acid-based antibacterial agents, which are also known as new quinolones and have now become important cures for infectious diseases.

The recent emergence of drug-resistant bacteria, such as Methicillin-Resistant *Staphylococcus aureus* (MRSA), Penicillin-Resistant *Streptococcus pneumoniae* (PRSP), and Vancomycin-Resistant *Enterococcus* (VRE), most of which are gram-positive bacteria, has posed a serious threat to the treatment of patients. Traditional quinolone carboxylic acid-based antibacterial agents have relatively weak antibacterial activities against gram-positive bacteria and thus are not considered as effective cures for the drug-resistant bacteria. Furthermore, the increasing incidence of Quinolone-Resistant *Staphylococcus aureus* (QRSA) makes the use of these drugs even more difficult.

While pyridobenzoxazine carboxylic acid-based antibacterial agents similar to the ones claimed in the present invention are described in, for example, Patent Articles 1, 2, and 3, none of these agents offer sufficient antibacterial activity against gram-positive bacteria, nor are they described to have antibacterial activity against drug-resistant bacteria such as those described above.

DISCLOSURE OF THE INVENTION

It is therefore an objective of the present invention to provide novel pyridobenzoxazine carboxylic acid-based compounds that, in addition to being safe and exhibiting strong antibacterial activities, are effective against drug-resistant bacteria that are less susceptible to conventional antibacterial agents.

In view of the above-described problems, the present inventors have devoted a significant amount of effort to seeking quinolone carboxylic acid derivatives that are effective against gram-positive bacteria, in particular, such drug-resistant bacteria as MRSA, PRSP, and VRE, which are less susceptible to traditional quinolone carboxylic acid-based antibacterial agents. The effort was rewarded by the discovery of the compounds of the present invention, which proved to be effective against gram-positive bacteria, in particular such drug-resistant bacteria as MRSA, PRSP, and VRE, and exhibit higher antibacterial activity as compared not only with traditional quinolone carboxylic acid-based antibacterial agents, but also with various other antibacterial agents. The discovery ultimately led the present inventors to complete the present invention.

According to the present invention, there is provided a compound as represented by the following general formula (I), or a salt or a hydrate thereof:

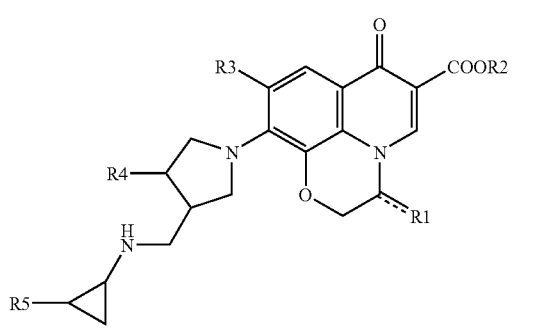

wherein R1 is a methyl group, a fluoromethyl group, a methoxymethyl group, an acetoxymethyl group, a hydroxymethyl group, or a methylene group; R2 is a hydrogen atom, a lower alkyl group having 1 to 3 carbon atoms, or a pharmaceutically acceptable cation and an ester of a prodrug; R3 is a hydrogen atom or a halogen atom; R4 is a hydrogen atom, a lower alkyl group having 1 to 3 carbon atoms, a fluoromethyl group, a trifluoromethyl group or a fluorine atom; and R5 is a hydrogen atom or a fluorine atom.

Examples of the lower alkyl group in the general formula (I) include a methyl group, an ethyl group, a propyl group, an isopropyl group, and a cyclopropyl group. Examples of the pharmaceutically acceptable cation include sodium ion, potassium ion, magnesium ion, calcium ion, and ammonium ion. Examples of the ester of a prodrug include a pivaloyloxymethyl group, an acetoxymethyl group, a phthalidinyl group, an indanyl group, a methoxymethyl group, and a 5-methyl-2-oxo-1, 3-dioxolene-4-yl group. Examples of the halogen atom include fluorine, chlorine, bromine, and iodine.

BEST MODE FOR CARRYING OUT THE INVENTION

An exemplary production process of the compound of the present invention will now be described.

The compound of the present invention may be produced by reacting a compound represented by the following general formula (II):

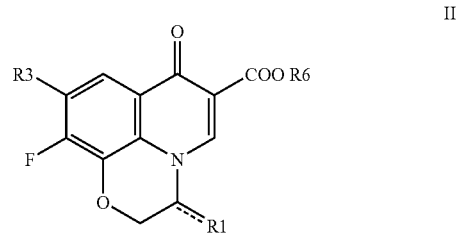

[wherein R1 and R3 are the same as in the general formula (I); and R6 is represented by the following general formula (III):

[wherein R6 and R7 are each independently a fluorine atom, or a lower alkylcarbonyloxy group]]

with a compound represented by the following general formula (IV), or an acid addition salt thereof:

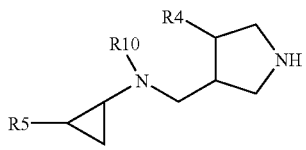

[wherein R4 and R5 are the same as in the general formula (I); and R10 is a hydrogen atom or a protective group of nitrogen atom such as t-butoxycarbonyl]

and then removing the boron chelate and, if necessary, the protective group of nitrogen atom.

The reaction of the compound of the general formula (II) with the compound of the general formula (IV) may be carried out in the absence or presence of a solvent, such as an alcohol, acetonitrile, dimethylsulfoxide, N,N-dimethylformamide, N,N-dimethylacetamide, N-methylpyrrolidone, tetrahydrofuran, dioxane, benzene, or toluene, and in the presence of an acid receptor. The acid receptor may be a carbonate or a hydrogen carbonate of an alkali metal or an alkaline earth metal, or a basic organic compound, such as triethylamine, diazabicyclo-7-undecene, or pyridine. The reaction is typically carried out at a temperature in the range of room temperature to 200° C. and preferably in the range of 25° C. to 150° C. The reaction takes from 30 min to 48 hours and is typically complete within 30 min to 15 hours.

If desired, the compound of the general formula (I) may be converted to its salt using an ordinary technique. Examples of such salts include salts formed with an inorganic acid, such as hydrochloric acid, sulfuric acid, and phosphoric acid, salts formed with an organic acid, such as methanesulfonic acid, lactic acid, oxalic acid, and acetic acid, and salts formed with sodium, potassium, magnesium, calcium, aluminum, cerium, chromium, cobalt, copper, iron, zinc, platinum, silver, or the like.

The compound of the present invention may be administered to humans or animals in a pharmaceutically known form through a pharmaceutically known route. For example, the compound may be prepared in the form of powders, tablets, capsules, ointments, injections, syrups, solutions, eye drops, and suppositories for oral or parenteral administration.

EXAMPLES

Exemplary tests as well as production processes for the compound of the present invention will now be described in detail with reference to examples.

Reference Example 1

Bis(acetato-O)[(3R)-9,10-difluoro-3-fluoromethyl-2, 3-dihydro-7-oxo-7H-pyrido [1,2,3-d,e][1,4]benzoxazine-6-carboxylato-$O^6,O^7$]boron To a mixture of boric acid (12.8 g) and acetic anhydride (63.4 g), zinc chloride (236 mg) was added and the resulting mixture was stirred at room temperature for 0.5 hours. To this mixture, (3R)-9,10-difluoro-3-fluoromethyl-2,3-dihydro-7-oxo-7H-pyrido [1,2,3-d,e][1,4]benzoxazine-6-carboxylic acid ethyl ester (22.6 g) was added and the mixture was stirred at 60° C. for 2.5 hours. Subsequently, the reaction mixture was concentrated under reduced pressure and the resulting residue was dissolved in ethyl acetate (300 mL). The solution was sequentially washed with a saturated aqueous solution of sodium hydrogen carbonate (2×200 mL) and then with water (100 mL), followed by drying over anhydrous sodium sulfate and concentration under reduced pressure. The resulting residue was purified on a silica gel column (dichloromethane: acetone=7:1), and the eluted yellow amorphous product was crystallized in an acetone/diethyl ether mixture to give 24.5 g of bis(acetato-O)[(3R)-9,10-difluoro-3-fluoromethyl-2,3-dihydro-7-oxo-7H-pyrido [1,2,3-d,e][1,4]benzoxazine-6-carboxylato-$O^6,O^7$]boron as a white powder.

$^1$H NMR(CDCl$_3$): δ 1.85 (s, 3H), 2.05 (s, 3H), 4.62 (ddd, J=2.9 Hz, 3.9 Hz, 12.2 Hz, 1H), 4.74 (ddd, J=7.8 Hz, 10.3 Hz, 46.4 Hz, 1H), 4.90 (ddd, J=4.9 Hz, 10.3 Hz, 45.4 Hz, 1H), 4.92 (dd, J=1.0 Hz, 12.7 Hz, 1H), 5.35–5.38 (m, 1H), 7.92 (dd, J=7.3 Hz, 9.3 Hz, 1H), 9.22 (s, 1H).

Elementary analysis (%): Calcd for $C_{17}H_{13}BF_3NO_8.0.75H_2O$: C, 46.34, H 3.32, N 3.18; found: C 46.30, H 3.34, N 3.30.

Reference Example 2

Synthesis of bis(acetato-O)[(3S)-9,10-difluoro-2,3-dihydro-3-methoxymethyl-7-oxo-7H-pyrido[1,2,3-d, e][1,4]benzoxazine-6-carboxylato-$O^6,O^7$]boron Step 1:
(3S)-9,10-Difluoro-2,3-dihydro-3-hydroxymethyl-7-oxo-7H-pyrido [1,2,3-d,e][1,4]benzoxazine-6-carboxylic acid ethyl ester (1.30 g) was suspended in anhydrous dimethylformamide (40 mL). Silver oxide (I) (4.63 g) and methyl iodide (1.25 mL) were then added to the suspension. The resulting mixture was stirred at room temperature for 21 hours. Subsequently, insoluble materials were removed from the reaction mixture by filtration and the filtrate was concentrated under reduced pressure. The resulting residue was purified on a silica gel column (dichloromethane: acetone=5: 1) to give 740 mg of (3S)-9, 10-difluoro-2,3-dihydro-3-methoxymethyl-7-oxo-7H-pyrido [1,2,3-d,e][1,4]benzoxazine-6-carboxylic acid ethyl ester as a white powder.

MS(EI) m/z: 339 (M$^+$).

Elementary analysis (%): Calcd for $C_{16}H_{15}F_2NO_5$: C 56.64, H 4.46, N 4.13; found: C 56.56, H 4.71, N 4.26.

Step 2:
In a similar manner to Reference Example 1, (3S)-9,10-difluoro-2,3-dihydro-3-methoxymethyl-7-oxo-7H-pyrido[1, 2,3-d,e][1,4]benzoxazine-6-carboxylic acid ethyl ester (679 mg) was reacted to give 830 mg of bis(acetato-O)[(3S)-9, 10-difluoro-2, 3-dihydro-3-methoxymethyl-7-oxo-7H-pyrido[1,2,3-d,e][1,4]benzoxazine-6-carboxylato-$O^6,O^7$]boron as a colorless amorphous product.

$^1$H NMR(CDCl$_3$): δ 1.86 (s, 3H), 2.06 (s, 3H), 3.39 (s, 3H), 3.70 (dd, J=8.3 Hz, 10.3 Hz, 1H), 3.82 (dd, J=5.4 Hz, 10.3 Hz, 1H), 4.56 (dd, J=2.9 Hz, 12.2 Hz, 1H), 4.86 (dd, J=1.0 Hz, 12.2 Hz, 1H), 5.10–5.13 (m, 1H), 7.89 (dd, J=7.3 Hz, 9.3 Hz, 1H), 9.13 (s, 1H).

Elementary analysis (%): Calcd for C$_{18}$H$_{16}$BF$_2$NO$_9$·1.5H$_2$O: C 46.38, H 4.11, N 3.00; found: C 46.18, H 3.74, N 3.15.

Reference Example 3

Synthesis of bis(acetato-O)[(3S)-3-acetoxymethyl-9,10-difluoro-2,3-dihydro-7-oxo-7H-pyrido[1,2,3-d,e][1,4]benzoxazine-6-carboxylato-$O^6,O^7$]boron Step 1:

(3S)-9,10-Difluoro-2,3-dihydro-3-hydroxymethyl-7-oxo-7H-pyrido[1,2,3-d,e][1,4]benzoxazine-6-carboxylic acid ethyl ester (976 mg) was suspended in anhydrous dichloromethane (30 mL). To the suspension, acetic anhydride (368 mg) and 4-dimethylaminopyridine (5.0 mg) were added and the resulting mixture was refluxed for 1.5 hours while heated. Subsequently, the mixture was allowed to cool and was washed with water. This was followed by drying over anhydrous sodium sulfate and concentration under reduced pressure. The resulting residue was suspended in ethanol and the suspension was filtrated to give 1.04 g of (3R)-3-acetoxymethyl-9,10-difluoro-2,3-dihydro-7-oxo-7H-pyrido[1,2,3-d,e][1,4]benzoxazine-6-carboxylic acid ethyl ester as a white powder.

MS(EI) m/z: 367(M$^+$).

Elementary analysis (%): Calcd for C$_{17}$H$_{15}$F$_2$NO$_6$: C 55.59, H 4.12, N 3.81; found: C 56.25, H 4.15, N 3.93.

Step 2:

In a similar manner to Reference Example 1, (3S)-3-acetoxymethyl-9,10-difluoro-2,3-dihydro-7-oxo-7H-pyrido[1,2,3-d,e][1,4]benzoxazine-6-carboxylic acid ethyl ester (918 mg) was reacted to give 1.00 g of bis(acetato-O)[(3S)-3-acetoxymethyl-9, 10-difluoro-2,3-dihydro-7-oxo-7H-pyrido[1,2,3-d,e][1,4]benzoxazine-6-carboxylato-$O^6,O^7$]boron as a colorless amorphous product.

$^1$H NMR(CDCl$_3$): δ 1.83 (s, 3H), 2.03 (s, 3H), 2.08 (s, 3H), 4.44–4.54 (m, 2H), 4.63 (dd, J=2.9 Hz, 12.2 Hz, 1H), 4.89 (dd, J=1.0 Hz, 12.7 Hz, 1H), 5.27–5.30 (m, 1H), 7.88 (dd, J=7.3 Hz, 9.3 Hz, 1H), 9.17 (s, 1H).

Elementary analysis (%): Calcd for C$_{19}$H$_{16}$BF$_2$NO$_{10}$·1.75H$_2$O: C 45.76, H 3.94, N 2.81; found: C 45.94, H 3.82, N 2.95.

Reference Example 4

Synthesis of trans-3-cyclopropylaminomethyl-4-methylpyrrolidine

Step 1:

trans-1-Benzyl-4-methyl-3-pyrrolidinecarboxylic acid (4.04 g) was dissolved in dichloromethane (50 mL). To this solution, 1,1'-carbonylbis-1H-imidazole (3.58 g) was added and the mixture was stirred at room temperature for 1 hour. While the reaction mixture was cooled on an ice bath, a dichloromethane solution (15 mL) of cyclopropylamine (1.53 mL) was added dropwise and the mixture was stirred at room temperature for 3 hours. Subsequently, the reaction mixture was washed with water, was dried over anhydrous sodium sulfate, and was then concentrated under reduced pressure. The resulting residue was crystallized in a hexane/diisopropyl ether mixture and the formed crystal was filtrated. The collected crystal was then washed with a hexane/diisopropyl ether mixture and was dried under reduced pressure to obtain 4.07 g of trans-1-benzyl-N-cyclopropyl-4-methyl-3-pyrrolidinecarboxamide as a white crystal.

Melting point: 81–83° C.

MS (EI) m/z: 258(M$^+$).

Step 2:

trans-1-Benzyl-N-cyclopropyl-4-methyl-3-pyrrolidinecarboxamide (3.80 g) was suspended in anhydrous tetrahydrofuran (85 mL). To this suspension, a 1mol/L tetrahydrofuran solution of borane-tetrahydrofuran complex (58.8 mL) was added and the mixture was refluxed for 8 hours while heated. Subsequently, a 2mol/L aqueous solution of sodium hydroxide (35 mL) was added to the reaction mixture and the mixture was refluxed for 4 hours while heated. After concentration under reduced pressure, the resultant residue was extracted with toluene (2×100 mL) and the toluene extracts were combined. The combined extract was washed with water, was dried over anhydrous sodium sulfate, and was then concentrated under reduced pressure. The resulting residue was dissolved in dichloromethane (50 mL). To this solution, di-tert-butyl dicarbonate (3.53 g) was added and the mixture was stirred at room temperature for 4 hours. Subsequently, the reaction mixture was concentrated under reduced pressure and the resulting residue was purified on a silica gel column (hexane:ethyl acetate=4:1 shifted to 1:1) to obtain 3.07 g of trans-1-benzyl-3-[[(N-tert-butoxycarbonyl-N-cyclopropyl)amino]methyl]-4-methylpyrrolidine as a colorless oil.

MS (FAB$^+$) m/z: 345 (MH$^+$).

HRMS (FAB$^+$): Calcd for C$_{21}$H$_{33}$N$_2$O$_2$ (MH$^+$): 345.2542; found: 345.2505.

Step 3:

trans-1-Benzyl-3-[[(N-tert-butoxycarbonyl-N-cyclopropyl)amino]methyl]-4-methylpyrrolidine (3.00 g) was dissolved in ethanol (50 mL). To this solution, 7.5% palladium carbon (300 mg) was added and the mixture was stirred at room temperature for 6 hours under a hydrogen pressure of 3.9×10$^5$ Pa. Subsequently, the catalyst was removed from the reaction mixture by filtration and the collected catalyst was washed with ethanol. The filtrate and the washing solution were combined and the resulting residue was dried under reduced pressure to obtain 2.12 g of trans-3-[[(N-tert-butoxycarbonyl-N-cyclopropyl)amino]methyl]-4-methylpyrrolidine as a pale brown oil.

MS (FAB$^+$) m/z: 255 (MH$^+$).

HRMS (FAB$^+$): Calcd for C$_{14}$H$_{27}$N$_2$O$_2$ (MH$^+$): 255.2073; found: 255.2079.

Step 4:

trans-3-[[(N-tert-Butoxycarbonyl-N-cyclopropyl)amino]methyl]-4-methylpyrrolidine (2.07 g) was dissolved in dichloromethane (10 mL). While this solution was cooled on an ice bath, trifluoroacetic acid (5 mL) was added and the mixture was stirred at room temperature for 2 hours. After concentration under reduced pressure, the resulting residue was dissolved in tetrahydrofuran (6 mL) and the solution was allowed to stand for 13 hours at room temperature. The separated crystal was collected by filtration, followed by washing with tetrahydrofuran and drying under reduced pressure, to give 2.47 g of trans-3-cyclopropylaminomethyl-4-methylpyrrolidine trifluoroacetic acid salt. The salt product (2.37 g) was dissolved in water (5 mL), followed by addition of a 20% aqueous solution of sodium hydroxide to adjust the pH to 14. The solution was then extracted with diethyl ether (2×50 mL) and the extracts were combined. The combined extract was then dried over anhydrous sodium sulfate and was concentrated under reduced pressure. The resulting residue was purified by distillation under reduced pressure to obtain 660 mg of trans-3-cyclopropylaminomethyl-4-methylpyrrolidine.

$^1$H NMR(CDCl$_3$): δ 0.30–0.37 (m, 2H), 0.41–0.45(m, 2H), 1.04(d, J=6.3 Hz, 3H), 1.66–1.76(m, 4H), 2.08–2.13(m, 1H), 2.46(dd, J=7.3 Hz, 10.7 Hz, 1H), 2.57(dd, J=8.3 Hz, 11.7 Hz, 1H), 2.63(dd, J=6.3 Hz, 10.7 Hz, 1H), 2.80 (dd, J=5.4 Hz, 11.7 Hz, 1H), 3.10 (dd, J=6.8 Hz, 10.7 Hz, 1H), 3.14 (dd, J=7.3 Hz, 10.7 Hz, 1H).

Elementary analysis (%): Calcd for C$_9$H$_{18}$N$_2$.2CF$_3$COOH: C 40.84, H 5.27, N 7.33; found: C 40.90, H 5.47, N 7.37.

Reference Example 5

Synthesis of (3R,4R)-3-cyclopropylaminomethyl-4-methylpyrrolidine

Step 1:
(3R,4R)-1-Benzyl-4-methyl-3-pyrrolidinecarboxylic acid (6.27 g) was suspended in dichloromethane (250 mL). To this suspension, cyclopropylamine (1.76 mL) and hydrochloric acid 1-ethyl-(3-dimethylaminopropyl)carbodiimide (12.2 g) were sequentially added and the mixture was stirred at room temperature for 4 hours. Subsequently, the reaction mixture was washed with water, was dried over anhydrous sodium sulfate, and was then concentrated under reduced pressure. The resulting residue was purified on a silica gel column (ethyl acetate: methanol=10:1) to give 3.32 g of (3R,4R)-1-benzyl-N-cyclopropyl-4-methyl-3-pyrrolidinecarboxamide as a white crystal.

MS (EI) m/z: 258 (M$^+$).

Elementary analysis (%): Calcd for C$_{16}$H$_{22}$N$_2$O: C 74.38, H 8.58, N 10.84; found: C 74.46, H 8.67, N 10.72.

Step 2:
In a similar manner to Step 2 in Reference Example 4, (3R,4R)-1-benzyl-N-cyclopropyl-4-methyl-3-pyrrolidinecarboxamide (5.52 g) was reacted to give 4.16 g of (3R,4R)-1-benzyl-3-[[(N-tert-butoxycarbonyl-N-cyclopropyl)amino]methyl]-4-methylpyrrolidine as a pale brown oil.

MS (FAB$^+$) m/z: 345 (MH$^+$).

HRMS (FAB$^+$): Calcd for C$_{21}$H$_{33}$N$_2$O$_2$ (MH$^+$): 345.2542; found 345.2585.

Step 3:
In a similar manner to Step 3 in Reference Example 4, (3R,4R)-1-benzyl-3-[[(N-tert-butoxycarbonyl-N-cyclopropyl)amino]methyl]-4-methylpyrrolidine (4.00 g) was reacted to give 2.88 g of (3R,4R)-3-[[(N-tert-butoxycarbonyl-N-cyclopropyl)amino]methyl]-4-methylpyrrolidine.

MS (FAB$^+$) m/z: 255 (MH$^+$).

HRMS (FAB$^+$): Calcd for C$_{14}$H$_{27}$N$_2$O$_2$(MH$^+$): 255.2073; found: 255.2070.

Step 4:
In a similar manner to Step 4 in Reference Example 4, (3R,4R)-3-[[(N-tert-butoxycarbonyl-N-cyclopropyl)amino]methyl]-4-methylpyrrolidine (2.78 g) was reacted to give 730 mg of (3R,4R)-3-cyclopropylaminomethyl-4-methylpyrrolidine.

Specific rotation: +74.6° (c=0.648, methanol).

Elementary analysis (%): Calcd for C$_9$H$_{18}$N$_2$.2CF$_3$COOH: C 40.84, H 5.27, N 7.33; found: C 40.73, H 5.26, N 7.36.

Reference Example 6

Synthesis of (3S,4S)-3-cyclopropylaminomethyl-4-methylpyrrolidine

Step 1:
In a manner similar to Step 1 in Reference Example 5, (3S,4S)-1-benzyl-4-methyl-3-pyrrolidinecarboxylic acid (14.5 g) was reacted to give 6.33 g of (3S,4S)-1-benzyl-N-cyclopropyl-4-methyl-3-pyrrolidinecarboxamide as a pale brown crystal.

MS (EI) m/z: 258 (M$^+$).

Elementary analysis (%): Calcd for C$_{16}$H$_{22}$N$_2$O: C 74.38, H 8.58, N 10.84; found: C 74.64, H 8.66, N 10.71.

Step 2:
In a manner similar to Step 2 in Reference Example 4, (3S,4S)-1-benzyl-N-cyclopropyl-4-methyl-3-pyrrolidinecarboxamide (6.13 g) was reacted to give 4.67 g of (3S,4S)-1-benzyl-3-[[(N-tert-butoxycarbonyl-N-cyclopropyl)amino]methyl]-4-methylpyrrolidine as a pale brown oil.

MS (FAB$^+$) m/z: 345 (MH$^+$).

HRMS (FAB$^+$): Calcd for C$_{21}$H$_{33}$N$_2$O$_2$ (MH$^+$): 345.2542; found: 345.2547.

Step 3:
In a similar manner to Step 3 in Reference Example 4, (3S,4S)-1-benzyl-3-[[(N-tert-butoxycarbonyl-N-cyclopropyl)amino]methyl]-4-methylpyrrolidine (4.47 g) was reacted to give 3.05 g of (3S,4S)-3-[[(N-tert-butoxycarbonyl-N-cyclopropyl)amino]methyl]-4-methylpyrrolidine.

MS (FAB$^+$) m/z: 255 (MH$^+$).

HRMS (FAB$^+$): Calcd for C$_{14}$H$_{27}$N$_2$O$_2$ (MH$^+$): 255.2073; found 255.2075.

Step 4:
In a similar manner to Step 4 in Reference Example 4, (3S,4S)-3-[[(N-tert-butoxycarbonyl-N-cyclopropyl)amino]methyl]-4-methylpyrrolidine (2.85 g) was reacted to give 1.21 g of (3S,4S)-3-cyclopropylaminomethyl-4-methylpyrrolidine.

Specific rotation: −74.5°(c=0.62, methanol).

Elementary analysis (%): Calcd for C$_9$H$_{11}$N$_2$-2CF$_3$COOH: C, 40.84, H 5.27, N, 7.33; found: C, 40.80, H, 5.18, N, 7.39.

Reference Example 7

Synthesis of cis-3-cyclopropylaminomethyl-4-methylpyrrolidine

Step 1:
c is-1-Benzyl-3-hydroxy-4-methylpyrrolidine (6.81 g) was dissolved in dichloromethane (70 mL). While this solution was cooled on a dry ice/acetone bath, triethylamine (5.21 mL) was added. Methanesulfonyl chloride (2.89 mL) was then added dropwise and the mixture was further stirred for 1 hour. Following addition of water (50 mL), the temperature of the mixture was allowed to rise to room temperature and the dichloromethane layer was separated. The aqueous layer was extracted with dichloromethane (50 mL) and the extract was combined with the dichloromethane layer. The combined dichloromethane layer was then washed with water, followed by drying over anhydrous sodium sulfate and concentration under reduced pressure. The resulting residue was dissolved in acetonitrile (180 mL). To this solution, tetrabutylammonium cyanide (23.9 g) was added and the mixture was refluxed for 7 hours while heated. Subsequently, the reaction mixture was concentrated under reduced pressure and the resulting residue was dissolved in ethyl acetate (300 mL). The solution was washed with water, was dried over anhydrous sodium sulfate, and was concentrated under reduced pressure. The resulting residue was purified on a silica gel column (hexane:ethyl acetate=1:1) to give 4.61 g of cis-1-benzyl-4-methyl-3-pyrrolidinecarbonitrile as a brown oil.

IR (neat): 2240, 1496, 1454 $cm^{-1}$.

MS (EI) m/z: 200 ($M^+$).

Step 2:

Lithium aluminum hydride (80%, 3.89 g) was suspended in diethyl ether (90 mL). While the suspension was cooled on an ice bath, a diethyl ether solution (25 mL) of cis-1-benzyl-4-methyl-3-pyrrolidinecarbonitrile (4.11 g) was added dropwise and the mixture was stirred at room temperature for 1 hour. While the reaction mixture was cooled on an ice bath, a saturated aqueous solution of sodium hydrogen carbonate (8 mL) was carefully added dropwise. Following dilution with diethyl ether (100 mL), insoluble materials were collected by filtration and were washed with diethyl ether. The filtrate and the washing solution were combined and the combined solution was concentrated under reduced pressure. The resulting residue was purified on a silica gel column (hexane:ethyl acetate=1:1 shifted to ethyl acetate: methanol=10:1) to give 2.35 g of cis-1-benzyl-4-methyl-3-aminomethylpyrrolidine as a pale yellow oil.

$^1$H NMR($CDCl_3$): δ 0.94 (d, J=7.3 Hz, 3H), 1.09–1.66 (br, 2H), 2.03 (dd, J=7.3 Hz, 9.3 Hz, 1H), 2.11–2.26 (m, 2H), 2.31–2.42 (m, 1H), 2.58 (dd, J=8.3 Hz, 12.2 Hz, 1H), 2.82 (dd, J=5.9 Hz, 12.2 Hz, 1H), 2.96–3.02 (m, 2H), 3.60 (s, 2H), 7.21–7.35 (m, 5H).

Step 3:

cis-1-Benzyl-4-methyl-3-aminomethylpyrrolidine (1000 mg) was dissolved in methanol (10 mL). While this solution was cooled on an ice bath, benzaldehyde (0.50 mL) was added dropwise and the mixture was stirred at room temperature for 1 hour. Subsequently, sodium cyanoborohydride (184 mg) was added and the mixture was stirred at room temperature for 1.5 hours. This was followed by a second addition of sodium cyanoborohydride (123 mg) and stirring for additional 5.5 hours. Subsequently, a 2mol/L aqueous solution of sodium hydroxide (5 mL) was added to the reaction mixture and the mixture was refluxed for 2 hours while heated. Following concentration under reduced pressure, the resulting residue was extracted with toluene (2×30 mL) and the toluene extracts were combined. The combined toluene layer was then washed with water, followed by drying over anhydrous sodium sulfate and concentration under reduced pressure. The resulting residue was purified on a silica gel column (hexane:ethyl acetate=4:1) to give 690 mg of cis-1-benzyl-3-benzylaminomethyl-4-methylpyrrolidine as a pale yellow oil.

MS (EI) m/z: 294 ($M^+$).

HRMS (EI): Calcd for $C_{20}H_{26}N_2$($M^+$): 294.2096; found: 294.2110.

Step 4:

cis-1-Benzyl-3-benzylaminomethyl-4-methylpyrrolidine (680 mg) was dissolved in methanol (7 mL). To this solution, molecular sieves 3A (700 mg), acetic acid (1.32 mL), [1-(ethoxycyclopropyl)oxy]trimethylsilane (1.85 mL), and sodium cyanoborohydride (435 mg) were added and the mixture was refluxed for 4 hours while heated. Insoluble materials were collected by filtration and were washed with methanol. The filtrate and the washing solution were combined and the combined organic layer was concentrated under reduced pressure. To the resulting residue, water was added (5 mL), followed by addition of a 2mol/L aqueous solution of sodium hydroxide to make the mixture basic. The mixture was then extracted with toluene (2×50 mL) and the extracts were combined. The combined toluene layer was then washed with water, was dried over anhydrous sodium sulfate, and was then concentrated under reduced pressure. The resulting residue was purified on a silica gel column (hexane:ethyl acetate=4:1) to give 648 mg of cis-1-benzyl-3-(N-benzyl-N-cyclopropyl)aminomethyl-4-methylpyrrolidine as a colorless oil.

MS (EI) m/z: 334 ($M^+$).

HRMS (EI): Calcd for $C_{23}H_{30}N_2$($M^+$): 334.2409; found: 334.2403.

Step 5:

cis-1-Benzyl-3-(N-benzyl-N-cyclopropyl)aminomethyl-4-methylpyrrolidine (640 mg) was dissolved in ethanol (10 mL). To this solution, 10% palladium carbon (500 mg) and chloroform (0.77 mL) were added and the mixture was stirred at 50° C. for 7 hours under a hydrogen pressure of $3.9×10^5$ Pa. From the reaction mixture, the catalyst was collected by filtration and was washed with ethanol. The filtrate and the washing solution were combined and the combined organic layer was concentrated under reduced pressure. To the resulting residue, water (2 mL) was added, followed by addition of a 2mol/L aqueous solution of sodium hydroxide to make the mixture basic. Sodium chloride was then added to the mixture for salting out and the mixture was extracted with diethyl ether (2×25 mL). The diethyl ether extracts were combined and the combined diethyl ether layer was dried over anhydrous sodium sulfate and was concentrated under reduced pressure. The resulting residue was purified on a silica gel column (hexane:ethyl acetate=4:1 shifted to dichloromethane: methanol=10:1) to give 124 mg of cis-3-cyclopropylaminomethyl-4-methylpyrrolidine as a pale brown oil.

MS ($CI^+$) m/z: 155 ($MH^+$).

HRMS ($CI^+$): Calcd for $C_9H_{19}N_2$($MH^+$): 155.1548; found: 155.1553.

Reference Example 8

Synthesis of (3R,4S)-3-cyclopropylaminomethyl-4-methylpyrrolidine

Step 1:

(3R,4S)-1-Benzyl-3-hydroxy-4-methylpyrrolidine (4.00 g) was dissolved in dichloromethane (40 mL). While this solution was cooled on a dry ice/acetone bath, triethylamine (3.06 mL) was added. Methanesulfonyl chloride (1.70 mL) was then added dropwise and the mixture was further stirred for 1 hour. Following addition of water (40 mL), the temperature of the mixture was allowed to rise to room temperature and the dichloromethane layer was separated. The aqueous layer was extracted with dichloromethane (40 mL) and the extract was combined with the dichloromethane layer. The combined dichloromethane layer was then washed with water, followed by drying over anhydrous sodium sulfate and concentration under reduced pressure. The resulting residue was dissolved in N,N-dimethylformamide (120 mL). To this solution, tetrabutylammonium cyanide (5.53 g) and sodium cyanide (2.05 g) were added and the mixture was stirred at 80° C. for 13 hours. Subsequently, the reaction mixture was concentrated under reduced pressure and water (50 mL) was added to the resulting residue. The mixture was extracted with diethyl ether (2×200 mL). The diethyl ether extracts were combined and the combined extract was washed with a saturated aqueous solution of sodium chloride, followed by drying over anhydrous sodium sulfate and concentration under reduced pressure. The resulting residue was purified on a silica gel column (hexane: ethyl acetate=4:1) to give 3.32 g of (3R,4S)-1-benzyl-4-methyl-3-pyrrolidinecarbonitrile as a brown oil.

$^1$H NMR(CDCl$_3$): δ 1.22 (d, J=7.3 Hz, 3H), 2.12 (dd, J=8.3 Hz, 9.3 Hz, 1H), 2.45–2.57 (m, 1H), 2.60–2.67 (m, 1H), 2.99 (dd, J=7.3 Hz, 9.3 Hz, 1H), 3.09–3.19 (m, 2H), 3.62 (s, 2H), 7.25–7.35 (m, 5H).

MS(EI) m/z: 200 (M$^+$).

Step 2:

In a similar manner to Step 2 in Reference Example 7, (3R,4S)-1-benzyl-4-methyl-3-pyrrolidinecarbonitrile (3.20 g) was reacted to obtain 2.98 g of (3S,4S)-1-benzyl-4-methyl-3-aminomethylpyrrolidine.

$^1$H NMR(CDCl$_3$): δ 0.94 (d, J=7.3 Hz, 3H), 2.03 (dd, J=7.3 Hz, 9.3 Hz, 1H), 2.11–2.26 (m, 2H), 2.31–2.43 (m, 1H), 2.58 (dd, J=8.3 Hz, 12.2 Hz, 1H), 2.82 (dd, J=5.9 Hz, 12.2 Hz, 1H), 2.97–3.02 (m, 2H), 3.60 (s,2H), 7.22–7.33 (m, 5H).

Step 3:

In a similar manner to Step 3 in Reference Example 7, (3S,4S)-1-benzyl-4-methyl-3-aminomethylpyrrolidine (2.80 g) was reacted to give 3.49 g of (3R,4S)-1-benzyl-3-benzylaminomethyl-4-methyl-pyrrolidine.

MS (EI) m/z: 294 (M$^+$).

HRMS (EI): Calcd for C$_{20}$H$_{26}$N$_2$(M$^+$): 294.2096; found: 294.2072.

Step 4:

In a similar manner to Step 4 in Reference Example 7, (3R,4S)-1-benzyl-3-benzylaminomethyl-4-methylpyrrolidine (3.40 g) was reacted to give 3.72 g of (3R,4S)-1-benzyl-3-(N-benzyl-N-cyclopropyl)aminomethyl-4-methylpyrrolidine.

MS (FAB$^+$) m/z: 335 (MH$^+$).

HRMS (EI): Calcd for C$_{23}$H$_{31}$N$_2$(MH$^+$): 335.2487; found: 335.2503.

Step 5:

In a similar manner to Step 5 in Reference Example 7, (3R,4S)-1-benzyl-3-(N-benzyl-N-cyclopropyl)aminomethyl-4-methylpyrrolidine (3.60 g) was reacted to give 1.29 g of (3R,4S)-3-cyclopropylaminomethyl-4-methylpyrrolidine.

MS (CI$^+$) m/z: 155 (MH$^+$).

HRMS (CI$^+$): Calcd for C$_9$H$_{19}$N$_2$(MH$^+$): 155.1548; found: 155.1539.

Reference Example 9

Synthesis of (3S,4R)-3-cyclopropylaminomethyl-4-methylpyrrolidine

Step 1:

In a similar manner to Step 1 in Example 8, (3S,4R)-1-benzyl-3-hydroxy-4-methylpyrrolidine (4.62 g) was reacted to give 3.07 g of (3S,4R)-1-benzyl-4-methyl-3-pyrrolidinecarbonitrile.

$^1$H NMR(CDCl$_3$): δ 1.22 (d, J=6.8 Hz, 3H), 2.13 (t,J=9.3 Hz, 1H), 2.45–2.55 (m, 1H), 2.61–2.65 (m, 1H), 2.99 (dd, J=6.8 Hz, 9.3 Hz, 1H), 3.09–3.19 (m, 2H), 3.62 (s, 2H), 7.27–7.34 (m 5H).

Step 2:

In a similar manner to Step 2 in Reference Example 7, (3S,4R)-1-benzyl-4-methyl-3-pyrrolidinecarbonitrile (3.00 g) was reacted to give 1.44 g of (3R,4R)-1-benzyl-4-methyl-3-aminomethylpyrrolidine.

MS (EI) m/z: 204 (M$^+$).

HRMS (EI): Calcd for C$_{13}$H$_{20}$N$_2$(M$^+$): 204.1626; found: 204.1614.

Step 3:

In a similar manner to Step 3 in Reference Example 7, (3R,4R)-1-benzyl-4-methyl-3-aminomethylpyrrolidine (1.06 g) was reacted to give 1.20 g of (3S,4R)-1-benzyl-3-benzylaminomethyl-4-methylpyrrolidine.

MS (EI) m/z: 294 (M$^+$).

HRMS (EI): Calcd for C$_{20}$H$_{26}$N$_2$(M$^+$): 294.2096; found: 294.2106.

Step 4:

In a similar manner to Step 4 in Reference Example 7, (3S,4R)-1-benzyl-3-benzylaminomethyl-4-methylpyrrolidine (1.40 g) was reacted to give 1.55 g of (3S,4R)-1-benzyl-3-(N-benzyl-N-cyclopropyl)aminomethyl-4-methylpyrrolidine.

MS (FAB$^+$) m/z: 335 (MH$^+$).

HRMS (EI): Calcd for C$_{23}$H$_{31}$N$_2$(MH$^+$): 335.2487; found: 335.2498.

Step 5:

In a similar manner to Step 5 in Reference Example 7, (3S,4R)-1-benzyl-3-(N-benzyl-N-cyclopropyl)aminomethyl-4-methylpyrrolidine (700 mg) was reacted to give 215 mg of (3S,4R)-3-cyclopropylaminomethyl-4-methylpyrrolidine.

MS (CI$^+$) m/z: 155 (MH$^+$).

HRMS (CI$^+$): Calcd for C$_9$H$_{19}$N$_2$(MH$^+$): 155.1548; found: 155.1510.

Reference Example 10

Synthesis of trans-3-cyclopropylaminomethyl-4-trifluoromethylpyrrolidine

Step 1:

In a similar manner to Step 1 in Example 4, trans-1-benzyl-4-trifluoromethyl-3-pyrrolidinecarboxylic acid (3.00 g) was reacted to give 3.32 g of trans-1-benzyl-4-trifluoromethyl-3-pyrrolidinecarboxamide.

$^1$H NMR(CDCl$_3$): δ 0.42–0.46 (m, 2H), 0.75–0.79 (m, 2H), 2.64–2.78 (m, 4H), 2.82–2.86 (m, 1H), 2.95 (t, J=9.3

Hz, 1H), 3.10–3.22 (m, 1H), 3.59 (d, J=13.2 Hz, 1H), 3.68 (d, J=12.7 Hz, 1H), 6.34–6.53 (br, 1H), 7.26–7.36 (m, 5H).

Step 2:

In a similar manner Step 2 in Example 4, trans-1-benzyl-4-trifluoromethyl-3-pyrrolidinecarboxamide (3.21 g) was reacted to give 3.37 g of trans-1-benzyl-3-[[(N-tert-butoxycarbonyl-N-cyclopropyl)amino]methyl]-4-trifluoromethylpyrrolidine.

MS (FAB$^+$) m/z: 399 (MH$^+$).

HRMS (FAB$^+$): Calcd for $C_{21}H_{30}F_3N_2O_2$ (MH$^+$): 399.2259; found: 399.2254.

Step 3:

In a similar manner to Step 3 in Example 4, trans-1-benzyl-3-[[(N-tert-butoxycarbonyl-N-cyclopropyl)amino]methyl]-4-trifluoromethylpyrrolidine (3.27 g) was reacted to give 2.38 g of trans-3-[[(N-tert-butoxycarbonyl-N-cyclopropyl)amino]methyl]-4-trifluoromethylpyrrolidine.

MS (FAB$^+$) m/z: 309 (MH$^+$).

HRMS (FAB$^+$): Calcd for $C_{14}H_{24}F_3N_2O_2$(MH$^+$): 309.1790; found: 309.1783.

Step 4:

In a similar manner to Step 4 in Example 4, trans-3-[[(N-tert-butoxycarbonyl-N-cyclopropyl)amino]methyl]-4-trifluoromethylpyrrolidine (2.30 g) was reacted to give 992 mg of trans-3-cyclopropylaminomethyl-4-trifluoromethylpyrrolidine.

$^1$H NMR(CDCl$_3$): δ 0.29–0.33 (m, 2H), 0.42–0.46 (m, 2H), 2.10-2.15 (m, 1H), 2.30–2.39 (m, 1H), 2.41–2.53 (m, 1H), 2.62–2.71 (m, 2H), 2.83 (dd, J=6.3 Hz, 11.7 Hz, 1H), 3.10 (d, J=6.8 Hz, 2H), 3.18 (dd, J=7.8 Hz, 11.7 Hz, 1H).

Elementary analysis (%): Calcd for $C_9H_{15}F_3N_2.2CF_3COOH$: C, 35.79, H 3.93, N, 6.42; found: C, 35.82, H, 3.90, N, 6.59.

Reference Example 11

Synthesis of (3R,4S)-3-cyclopropylaminomethyl-4-fluoropyrrolidine (Process (I))

Step 1:

(E)-3-Benzyloxypropenyl-(1R)-camphorsultam (21.6 g) was dissolved in dichloromethane (300 mL) containing trifluoroacetic acid (0.116 mL). To this solution, N-methoxymethyl-N-(trimethylsilyl)benzylamine (15.0 g) was added dropwise and the mixture was further stirred for 2 hours. The mixture was sequentially washed with a saturated aqueous solution of sodium hydrogen carbonate (2×200 mL) and then with water (200 mL), followed by drying over anhydrous sodium sulfate and concentration under reduced pressure. The resulting pale yellow oil was dissolved in diethyl ether (150 mL) and the solution was allowed to stand for 18 hours at room temperature. The crystal formed was collected by filtration, was washed with diethyl ether, and was then dried under reduced pressure to give 11.5 g of N-[[(3S,4R)-benzyl-4-benzyloxypyrrolidin-3-yl]carbonyl]-(2'S)-bornane-10,2-sultam as a white crystal. The filtrate and the washing solution were combined and the combined organic layer was concentrated under reduced pressure. The resulting residue was purified on a silica gel column (eluant=cyclohexane:ethyl acetate=4:1) to obtain additional 8.48 g of N-[[(3S,4R)-benzyl-4-benzyloxypyrrolidin-3-yl]carbonyl]-(2'S)-bornane-10,2-sultam.

$^1$H NMR(CDCl$_3$): δ 0.95 (s, 3H), 1.02 (s, 3H), 1.32–1.45 (m, 2H), 1.86–1.96 (m, 3H), 2.00–2.10 (m, 2H), 2.57 (dd, J=9.3 Hz, 5.3 Hz), 2.69 (dd, J=9.8 Hz, 3.9 Hz, 1H), 2.93 (dd, J=10.3 Hz, 6.3 Hz, 1H), 3.20 (t, J=9.3 Hz), 3.42–3.51 (m, 3H), 3.69–3.74 (m, 2H), 3.90 (d, J=11.7 Hz), 4.54 (d, J=11.7 Hz), 4.63–4.66 (m, 1H), 7.22–7.31 (m, 10H).

Step 2:

Lithium aluminum hydride (80%, 5.56 g) was suspended in tetrahydrofuran (170 mL). While the suspension was cooled on a sodium chloride/ice bath, a tetrahydrofuran solution (300 mL) of N-[[(3S,4R)-benzyl-4-benzyloxypyrrolidin-3-yl]carbonyl]-(2'S)-bornane-10,2-sultam (19.9 g) was added dropwise and the mixture was stirred at −5° C. or below for 1 hour. Subsequently, water (34 mL) was carefully added dropwise to the mixture. Insoluble materials were collected by filtration and were washed with ethyl acetate (2×400 mL). The filtrate and the washing solutions were combined and the combined organic layer was extracted with 1 mol/L hydrochloric acid (2×500 mL). The hydrochloric acid extracts were combined and a 30% aqueous solution of sodium hydroxide was added to make the combined solution basic (pH 14). The mixture was then extracted with diethyl ether (2×500 mL) and the diethyl ether extracts were combined. The combined diethyl ether layer was concentrated under reduced pressure and the resulting residue was purified on a silica gel column (eluant=hexane:ethyl acetate=1:1) to give 9.91 g of (3R,4R)-(1-benzyl-4-benzyloxypyrrolidin-3-yl) methanol as a pale yellow oil.

$^1$H NMR(CDCl$_3$): δ 2.29–2.34(m, 1H), 2.40 (dd, J=10.3 Hz, 4.4 Hz, 1H), 2.68 (dd, J=9.3 Hz, 2.4 Hz, 1H), 2.75 (dd, J=9.8 Hz, 6.3 Hz, 1H), 3.18 (dd, J=9.8 Hz, 6.8 Hz, 1H), 3.61 (s, 2H), 3.65 (dd, J=10.3 Hz, 4.4 Hz, 1H), 3.73 (dd, J=10.3 Hz, 4.4 Hz, 1H), 4.07 (ddd, J=6.3 Hz, 4.4 Hz, 2.0 Hz, 1H), 4.48 (s, 2H), 7.25–7.35 (m, 10H).

Step 3:

Process (A): (3R,4R)-(1-benzyl-4-benzyloxypyrrolidin-3-yl)methanol (9.80 g) was dissolved in ethanol (100 mL). To this solution, 10% palladium carbon (2.00 g) was added and the mixture was stirred at 50° C. for 21 hours under a hydrogen pressure of $3.9×10^5$ Pa. Subsequently, the catalyst was collected from the reaction mixture by filtration through a Celite pad. The collected catalyst and the Celite pad were washed with ethanol. The filtrate and the washing solution were combined and the combined organic layer was concentrated under reduced pressure. The resulting residue was dissolved in ethanol (100 mL), followed by addition of 10% palladium carbon (2.00 g). The mixture was then stirred at 50° C. for 20 hours under a hydrogen pressure of $3.9×10^5$ Pa. Subsequently, the catalyst was collected from the reaction mixture by filtration through a Celite pad. The collected catalyst and the Celite pad were washed with ethanol. The filtrate and the washing solution were combined and the combined organic layer was concentrated under reduced pressure. The resulting residue was dried under reduced pressure to give 3.77 g of (3R,4R)-(4-hydroxypyrrolidin-3-yl)methanol.

$^1$H NMR (DMSO-d$_6$): δ 1.96–2.03 (m, 1H), 2.61 (dd, J=11.6 Hz, 5.5 Hz, 1H), 2.68 (dd, J=11.6 Hz, 3.1 Hz, 1H), 2.91 (dd, J=11.1 Hz, 5.5 Hz, 1H), 3.06 (dd, J=11.0 Hz, 7.3 Hz, 1H), 3.26 (dd, J=10.4 Hz, 7.3 Hz, 1H), 3.37 (dd, J=10.4 Hz, 6.1 Hz), 3.90–3.93 (m, 1H).

Sodium hydroxide (2.70 g) was dissolved in water (25 mL) and dioxane (15 mL) was added. To this solution, (3R,4R)-(4-hydroxypyrrolidin-3-yl)methanol (1.00 g) was dissolved. While the solution was cooled on an ice bath, carbobenzoxy chloride (0.97 mL) was added dropwise. The mixture was stirred at 5° C. or below for 1 hour, followed by dropwise addition of carbobenzoxy chloride (0.97 mL). The mixture was further stirred at 5° C. or below for additional 1 hour and carbobenzoxy chloride (0.97 mL) was subsequently added dropwise. This was followed by stirring for 1 hour at 5° C. or below and another 1 hour at room temperature. Subsequently, the reaction mixture was extracted with dichloromethane (2×100 mL). The dichloromethane extracts were combined, and the combined dichloromethane layer was dried over anhydrous sodium sulfate and was concentrated under reduced pressure. The resulting residue was purified on a silica gel column (eluant=hexane:ethyl acetate=1:1 shifted to ethyl acetate: methanol=20:1) to give 1.18 g of (3R,4R)-[1-benzyloxycarbonyl-4-hydroxypyrrolidin-3-yl]methanol as a milky white tar-like product.

MS (EI) m/z: 251 (M$^+$).

$^1$H NMR(CDCl$_3$): δ 2.08–2.40 (br +m, 2H), 2.58–2.79 (br, 1H), 3.20 (dd, J=11.0 Hz, 7.3 Hz, 1H), 3.32 (dt, J=11.1 Hz, 5.5 Hz, 1H), 3.59–3.76 (m, 4H), 4.23–4.33 (br, 1H), 5.12 (s, 2H), 7.28–7.36 (m, 5H).

Process (B): (3R,4R)-[1-benzyl-4-benzyloxypyrrolidin-3-yl]methanol (10.0 g) was dissolved in methanol (200 mL). To this solution, 10% palladium carbon (3.00 g) suspended in water (60 mL) and ammonium formate (21.2 g) were sequentially added, and the mixture was heat-refluxed for 4 hours while being stirred. Subsequently, the catalyst was collected from the reaction mixture by filtration through a Celite pad. The collected catalyst and the Celite pad were washed with a methanol/water mixture (80:20). The filtrate and the washing solution were combined and the combined solution was concentrated under reduced pressure. The resulting pale brown, tar-like material was dissolved in N,N-dimethylformamide (100 mL). While this solution was cooled on an ice bath, triethylamine (9.40 mL) was added, followed by dropwise addition of carbobenzoxy chloride (6.00 mL). While being cooled on an ice bath, the resulting mixture was stirred for 1.5 hours and was subsequently concentrated under reduced pressure. The resulting residue was dissolved in ethyl acetate (400 mL) and the solution was washed with a saturated aqueous solution of sodium chloride (2×100 mL), was dried over anhydrous sodium sulfate, and was then concentrated under reduced pressure. The resulting residue was purified on a silica gel column (eluant=ethyl acetate, shifted to ethyl acetate: methanol=20:1) to give 7.66 g of (3R,4R)-[1-benzyloxycarbonyl-4-hydroxypyrrolidin-3-yl]methanol as a milky white tar-like product.

This compound was identical to the compound obtained by Process (A).

Step 4:

Process (A): (3R,4R)-(1-benzyloxycarbonyl-4-hydroxypyrrolidin-3-yl)methanol (3.19 g) was dissolved in N,N-dimethylformamide (91 mL). While this solution was cooled on an ice bath, imidazole (6.05 g) and tert-butylchlorodimethylsilane (5.74 g) were sequentially added and the mixture was stirred at room temperature for 3 hours. Subsequently, the reaction mixture was concentrated under reduced pressure and the resulting residue was dissolved in diethyl ether (400 mL). The diethyl ether layer was washed with a saturated aqueous solution of sodium chloride (2×100 mL), was dried over anhydrous sodium sulfate, and was then concentrated under reduced pressure. The resulting residue was purified on a silica gel column (eluant=hexane:ethyl acetate=4:1) to give 5.46 g of (3R,4R)-1-benzyloxycarbonyl-3-(tert-butyldimethylsilyl)oxymethyl-4-(tert-butyldimethylsilyl)oxypyrrolidine as a colorless oil.

MS (CI$^+$): m/z=480 (MH$^+$).

$^1$H NMR(CDCl$_3$): δ 0.03 (s, 3H), 0.05 (s, 3H), 0.06 (s, 3H), 0.07 (s, 3H), 0.87 (s, 9H), 0.88 (s, 9H), 2.17–2.27 (m, 1H), 3.21–3.28 (m, 2H), 3.48–3.67 (m, 4H), 4.21–4.28 (m, 1H), 5.13 (s, 2H), 7.31–7.37 (m, 5H).

(3R,4R)-1-Benzyloxycarbonyl-3-(tert-butyldimethylsilyl)oxymethyl-4-(tert-butyldimethylsilyl)oxypyrrolidine (5.46 g) was dissolved in tetrahydrofuran (23 mL). While this solution was cooled on an ice bath, water (23 mL) and acetic acid (68 mL) were sequentially added and the mixture was stirred at room temperature for 8 hours. Subsequently, the reaction mixture was concentrated under reduced pressure and the resulting residue was purified on a silica gel column (eluant=hexane:ethyl acetate=4:1 shifted to 1:1) to give 2.74 g of (3R,4R)-1-benzyloxycarbonyl-3-hydroxymethyl-4-(tert-butyldimethylsilyloxy)pyrrolidine as a colorless oil.

MS (CI$^+$): m/z=366(MH$^+$).

$^1$H NMR(CDCl$_3$): δ 0.07–0.08 (m, 6H), 0.88 (s, 9H), 2.23–2.35 (m, 1H), 3.21–3.30 (m, 2H), 3.58–3.72 (m, 4H), 4.17–4.25 (m, 1H), 5.128 (s, 1H), 5.135 (s, 1H), 7.31–7.37 (m, 5H).

(3R,4R)-1-Benzyloxycarbonyl-3-hydroxymethyl-4-(tert-butyldimethylsilyloxy)pyrrolidine (2.73 g) was dissolved in dichloromethane (60 mL). While this solution was cooled on a sodium chloride/ice bath, triethylamine (1.21 mL) was added, which was followed by dropwise addition of methanesulfonyl chloride (0.71 mL) at −5° C. or below. The reaction mixture was then stirred at −5° C. or below for 1 hour, was washed with water (2×25 mL), was dried over anhydrous sodium sulfate, and was then concentrated under reduced pressure. The resulting residue was dissolved in N,N-dimethylformamide (60 mL), followed by addition of sodium azide (1.14 g) and stirring at 100° C. for 2 hours. The reaction mixture was then concentrated under reduced pressure and water (30 mL) was added to the resulting residue. The mixture was then extracted with diethyl ether (2×100 mL) and the diethyl ether extracts were combined. The combined diethyl ether layer was dried over anhydrous sodium sulfate and was concentrated under reduced pressure. The resulting residue was purified on a silica gel column (eluant=hexane:ethyl acetate=4:1) to give 3.06 g of (3R,4R)-3-azidomethyl-1-benzyloxycarbonyl-4-(tert-butyldimethylsilyl)oxypyrrolidine as a colorless oil.

MS (CI$^+$):m/z=391 (MH$^+$).

$^1$H NMR(CDCl$_3$): δ 0.07–0.09 (m, 3H), 2.23–2.34 (m, 1H), 3.19–3.25 (m, 2H), 3.27–3.40 (m, 2H), 3.60–3.71 (m, 2H), 4.11–4.17 (m, 1H), 5.13 (s, 2H), 7.31–7.37 (m, 5H).

(3R,4R)-3-Azidomethyl-1-benzyloxycarbonyl-4-(tert-butyldimethylsilyl)oxypyrrolidine (3.05 g) was dissolved in tetrahydrofuran (50 mL). While this solution was cooled on an ice bath, tetrabutylammonium fluoride (1mol/L tetrahydrofuran solution, 13.3 mL) was added dropwise and the mixture was stirred for additional 1 hour. Subsequently, a saturated aqueous solution of sodium chloride 70 mL) was added and the mixture was extracted with ethyl acetate (150 mL, 100 mL). The ethyl acetate extracts were combined and the combined solvent was dried over anhydrous sodium sulfate and was concentrated under reduced pressure. The resulting residue was purified on a silica gel column (eluant=ethyl acetate) to give 2.01 g of (3R,4R)-3-azidomethyl-1-benzyloxycarbonyl-4-hydroxypyrrolidine as a milky white syrup-like product.

MS (CI$^+$):m/z=277 (MH$^+$).

$^1$H NMR (CDCl$_3$): δ 2.18–2.30 (br, AH), 2.32–2.40 (m, 1H), 3.24 (dd, J=11.6 Hz, 6.1 Hz, 1H), 3.30–3.47 (m, 3H), 3.68–3.75 (m, 2H), 4.18–4.24 (m, 1H), 5.13 (s, 2H), 7.31–7.37 (m, 5H).

Process (B): (3R,4R)-[1-Benzyloxycarbonyl-4-hydroxypyrrolidin-3-yl]methanol (3.00 g), sodium azide (2.32 g), triphenylphosphine (3.43 g) and N,N-dimethylformamide (60 mL) were mixed with each other. While the mixture was cooled on an ice bath, a dichloromethane solution (14 mL) of carbon tetrabromide (4.34 g) was added dropwise. The reaction mixture was stirred for 25 hours at room temperature and additional 2 hours at 60° C., followed by addition of methanol (5 mL) and concentration under reduced pressure. The resulting residue was dissolved in ethyl acetate (200 mL) and was washed with a saturated aqueous solution of sodium chloride (2×50 mL), followed by drying over anhydrous sodium sulfate and concentration under reduce pressure. The resulting residue was purified on silica gel column (eluant=ethyl acetate:hexane=2:1) to give 2.94 g of (3R,4R)-3-azidomethyl-1-benzyloxycarbonyl-4-hydroxypyrrolidine as a pale brown syrup-like product. This compound was identical to the compound obtained by Process (A).

Process (C): (3R,4R)-[1-Benzyloxycarbonyl-4-hydroxypyrrolidin-3-yl]methanol (150 mg) was dissolved in dichloromethane (12 mL) and 2,4,6-collidine (0.79 mL) was added. While this solution was cooled on an ice bath, methanesulfonyl chloride (46.2 μL) was added dropwise. The mixture was then stirred for 2 hours on the ice bath and was allowed to stand for 15 hours in a refrigerator (3° C.). Subsequently, the reaction mixture was sequentially washed with water (2 mL), 1 mol/L hydrochloric acid (2×2 mL), and a saturated aqueous solution of sodium chloride (2×2 mL), followed by drying over anhydrous sodium sulfate and concentration under reduced pressure. The resulting residue was purified on a silica gel column (eluant=hexane:ethyl acetate=1:2 shifted to ethyl acetate) to give 38.7 mg of (3R,4R)-1-benzyloxycarbonyl-3-methanesulfonyloxy-4-methanesulfonyloxymethylpyrrolidine as a pale yellow syrup-like product and 133 mg of (3R,4R)-1-benzyloxycarbonyl-3-hydroxy-4-methanesulfonyloxymethylpyrrolidine as a white syrup-like product.

(3R,4R)-1-Benzyloxycarbonyl-3-hydroxy-4-methanesulfonyloxymethylpyrrolidine (125 mg) was dissolved in N,N-dimethylformamide (3 mL) and sodium azide (50.0 mg) was added. The mixture was stirred at 100° C. for 1 hour and was then concentrated under reduced pressure. The resulting residue was dissolved in ethyl acetate (5 mL) and the solution was washed with water (2×1 mL), followed by drying over anhydrous sodium sulfate and concentration under reduced pressure. The resulting residue was purified on a silica gel column (eluant=ethyl acetate) to give 91.0 mg of (3R,4R)-3-azidomethyl-1-benzyloxycarbonyl-4-hydroxypyrrolidine as a milky white syrup-like product. The compound was identical to the compound obtained by Process (A).

Step 5:

Process (A): (3R,4R)-3-Azidomethyl-1-benzyloxycarbonyl-4-hydroxypyrrolidine (1.20 g) was dissolved in dichloromethane (40 mL). While this solution was cooled on a sodium chloride/ice bath, diethylaminosulfur trifluoride (1.20 mL) was added dropwise and the mixture was stirred at room temperature for 3 hours. The reaction vessel was again cooled on a sodium chloride/ice bath and diethylaminosulfur trifluoride (0.57 mL) was again added dropwise. The mixture was then stirred at room temperature for 2 hours. While the reaction mixture was cooled on an ice bath, a saturated aqueous solution of sodium hydrogen carbonate (40 mL) was added dropwise and the dichloromethane layer was separated. The dichloromethane layer was sequentially washed with a saturated aqueous solution of sodium hydrogen carbonate (2×20 mL) and water (20 mL), followed by drying over anhydrous sodium sulfate and concentration under reduced pressure. The resulting residue was purified on a silica gel column (eluant=hexane:ethyl acetate=2:1) to give 726 mg of (3R,4S)-3-azidomethyl-1-benzyloxycarbonyl-4-fluoropyrrolidine as a pale brown oil.

MS (CI$^+$):m/z=279 (MH$^+$).

$^1$H NMR(CDCl$_3$): δ 2.34–2.54 (m, 1H), 3.22 (dt, J=11.0 Hz, 2.4 Hz, 1H), 3.39–3.49 (m, 1H), 3.54–3.69 (m, 2H), 3.73–3.91 (m, 2H), 5.14 (s, 2H), 5.16 (dt, J=53.2 Hz, 3.7 Hz, 1H), 7.32–7.37 (m, 5H).

Process (B): (3R,4R)-3-Azidomethyl-1-benzyloxycarbonyl-4-hydroxypyrrolidine (1.79 g) was dissolved in toluene (56 mL). While this solution was cooled on an ice bath, 1,8-diazabicyclo[5.4.0]undec-7-ene (2.03 mL) was added. This was followed by dropwise addition of perfluoro-1-octanesulfonyl fluoride (2.80 mL) and stirring for another 1 hour. Insoluble materials were removed from the reaction mixture by filtration and were washed with toluene. The filtrate and the washing solution were combined and the combined organic layer was concentrated under reduced pressure. The resulting residue was then purified on a silica gel column (eluant=hexane:ethyl acetate=2:1) to give 1.58 g of (3R,4S)-3-azidomethyl-1-benzyloxycarbonyl-4-fluoropyrrolidine as a pale brown syrup-like product. The compound was identical to the compound obtained by Process (A).

Step 6:

(3R,4S)-3-Azidomethyl-1-benzyloxycarbonyl-4-fluoropyrrolidine (1.35 g) was dissolved in ethanol (30 mL). To this solution, platinum oxide (IV) (190 mg) was added and the mixture was stirred at room temperature for 2 hours in a stream of hydrogen (provided from a balloon). Subsequently, the catalyst was collected from the reaction mixture by filtration through a Celite pad. The collected catalyst and the Celite pad were washed with ethanol. The filtrate and the washing solution were combined and the combined organic layer was concentrated under reduced pressure. The resulting residue was purified on a silica gel column (eluant=ethyl acetate: methanol=10:1) to give 1.13 g of (3S,4S)-3-aminomethyl-1-benzyloxycarbonyl-4-fluoropyrrolidine as a pale brown oil.

MS (CI$^+$):m/z=253 (MH$^+$).

Step 7:

(3S,4S)-3-Aminomethyl-1-benzyloxycarbonyl-4-fluoropyrrolidine (1.10 g) was dissolved in methanol (13 mL). To this solution, molecular sieves 4A (440 mg) and benzaldehyde (0.44 mL) were sequentially added and the mixture was stirred at room temperature for 1 hour. Subsequently, a borane-pyridine complex (0.44 mL) was added and the mixture was further stirred at room temperature for 3.5 hours. This was followed by addition of 6 mol/L hydrochloric acid (7.3 mL) and stirring at room temperature for 1 hour. Subsequently, a 30% aqueous solution of sodium hydroxide was added to make the mixture basic and the mixture was extracted with diethyl ether (2×100 mL). The diethyl ether extracts were combined and the combined diethyl ether layer was dried over anhydrous sodium sulfate and was then concentrated under reduced pressure. The resulting residue was purified on a silica gel column (eluant=hexane:ethyl acetate=4:1 shifted to 1:1) to give 1.18 g of (3S,4S)-3-benzylaminomethyl-1-benzyloxycarbonyl-4-fluoropyrrolidine as a colorless tar-like product.

MS (CI$^+$):m/z=343 (MH$^+$).

Step 8:

(3S,4S)-3-Benzylaminomethyl-1-benzyloxycarbonyl-4-fluoropyrrolidine (1.15 g) was dissolved in methanol (21 mL). To this solution, molecular sieves 3A (1.05 g), acetic acid (1.92 mL), [(1-ethoxycyclopropyl)oxy]trimethylsilane (2.70 mL), and sodium cyanoborohydride (633 mg) were added and the mixture was heat-refluxed for 2 hours while being stirred. Subsequently, insoluble materials were removed from the reaction mixture by filtration through a Celite pad. The insoluble materials and the Celite pad were washed with methanol. The filtrate and the washing solution were combined and a 2mol/L aqueous solution of sodium hydroxide was added to make the combined organic layer basic (pH14). Methanol was then removed under reduced pressure and the residue was extracted with diethyl ether (2×100 mL). The diethyl ether extracts were combined and the combined diethyl ether layer was dried over anhydrous sodium sulfate and was then concentrated under reduced pressure. The resulting residue was purified on a silica gel column (eluant=hexane:ethyl acetate=4:1) to give 1.26 g of (3S,4S)-3-(N-benzyl-N-cyclopropyl)aminomethyl-1-benzyloxycarbonyl-4-fluoropyrrolidine as a colorless tar-like product.

MS (EI) m/z:=382 ($M^+$).

Step 9:

(3S,4S)-3-(N-Benzyl-N-cyclopropyl)aminomethyl-1-benzyloxycarbonyl-4-fluoropyrrolidine (1.22 g) was dissolved in ethanol (14 mL). To this solution, 10% palladium carbon (150 mg) was added and the mixture was stirred at room temperature for 4 hours in a stream of hydrogen (provided from a balloon). Subsequently, the catalyst was collected from the reaction mixture by filtration through a Celite pad. The collected catalyst and the Celite pad were washed with ethanol. The filtrate and the washing solution were combined and the combined organic layer was concentrated under reduced pressure. The resulting residue was purified on a silica gel column (eluant=ethyl acetate:methanol=20:1). The eluate was distilled under reduced pressure to give 414 mg of (3R,4S)-3-cyclopropylaminomethyl-4-fluoropyrrolidine as a colorless oil.

MS ($CI^+$): m/z=159 ($MH^+$).

HRMS ($CI^+$): Calcd for $C_8H_{16}FN_2$: 159.1298; found: 159.1316.

Reference Example 12

Synthesis of (3R,4S)-3-cyclopropylaminomethyl-4-fluoropyrrolidine (Process (II))

Step 1:

(3R,4R)-(4-Hydroxypyrrolidin-3-yl)methanol (1.18 g) was dissolved in ethanol (25 mL) and triethylamine (1.40 mL) was added to the solution. While this mixture was cooled on a sodium chloride/ice bath, benzyl bromide (1.10 mL) was added dropwise. The mixture was then stirred at room temperature for 1 hour and was concentrated under reduced pressure. The resulting residue was purified on a silica gel column (eluant=ethyl acetate:methanol=20:1) to give 1.02 g of (3R,4R)-(1-benzyl-4-hydroxypyrrolidin-3-yl)methanol as a milky white syrup-like product.

MS ($EI^+$): m/z=207 ($M^+$).

HRMS ($EI^+$): Calcd for $C_{12}H_{17}NO_2$: 207.1259; found: 207.1237.

Step 2:

(3R,4R)-(1-Benzyl-4-hydroxypyrrolidin-3-yl)methanol (1.36 g) was dissolved in dichloromethane (14 mL). While this solution was cooled on an dry ice/acetone bath, triethylamine (0.83 mL) was added, followed by dropwise addition of methanesulfonyl chloride (0.46 mL) and stirring for 30 min. Water (10 mL) was then added to the reaction mixture and the temperature of the mixture was allowed to rise to room temperature. The mixture was then diluted with dichloromethane (20 mL) and the dichloromethane layer was collected. The collected dichloromethane layer was washed with water (2×10 mL), was dried over anhydrous sodium sulfate, and was then concentrated under reduced pressure. The resulting residue was purified on a silica gel column (hexane:ethyl acetate=1:1 shifted to ethyl acetate:methanol=20:1). From a fraction eluted at hexane:ethyl acetate=1:1, 585 mg of (3R,4R)-1-benzyl-3-methanesulfonyloxy-4-methanesulfonyloxymethylpyrrolidine was obtained as a milky white syrup-like product.

MS ($EI^+$): m/z=363 ($M^+$).

HRMS ($EI^+$): Calcd for $C_{14}H_{21}NO_6S_2$: 363.0810; found: 363.0804.

Also, 840 mg of (3R,4R)-1-benzyl-3-hydroxy-4-methanesulfonyloxymethylpyrrolidine was obtained as a white crystal from a fraction eluted at ethyl acetate:methanol=20:1.

MS ($EI^+$): m/z=285 ($M^+$).

HRMS ($EI^+$): Calcd for $C_{13}H_{19}NO_4S$: 285.1035; found: 285.1045.

Step 3:

(3R,4R)-1-Benzyl-3-hydroxy-4-methanesulfonyloxymethylpyrrolidine (835 mg), sodium azide (381 mg), and N,N-dimethylformamide (12 mL) were mixed with one another and the mixture was stirred at 120° C. for 1 hour. Subsequently, the reaction mixture was concentrated under reduced pressure. To the resulting residue, water (10 mL) was added and the mixture was extracted with diethyl ether (2×30 mL). The diethyl ether extracts were combined and the combined extract was dried over anhydrous sodium sulfate and was concentrated under reduced pressure. The resulting residue was purified on a silica gel column (eluant=ethyl acetate:methanol=20:1) to give 576 mg of (3R,4R)-3-azidomethyl-1-benzyl-4-hydroxypyrrolidine as a pale brown oil.

MS ($EI^+$): m/z=232 ($M^+$).

HRMS ($EI^+$): Calcd for $C_{12}H_{16}N_4O$: 232.1324; found: 232.1309.

Step 4:

(3R,4R)-3-Azidomethyl-1-benzyl-4-hydroxypyrrolidine (566 mg) was dissolved in dichloromethane (9 mL). While this solution was cooled on an ice bath, diethylaminosulfur trifluoride (0.39 mL) was added dropwise and the mixture was stirred at room temperature for 2 hours. While the reaction vessel was cooled on an ice bath, a saturated aqueous solution of sodium hydrogen carbonate (9 mL) was added, and the mixture was diluted with dichloromethane (15 mL). The dichloromethane layer was collected and the collected dichloromethane layer was washed with a saturated aqueous solution of sodium hydrogen carbonate (10 mL) and then water (10 mL), was dried over anhydrous sodium sulfate, and was concentrated under reduced pressure. The resulting residue was purified on a silica gel column (eluant=hexane:ethyl acetate=4:1). From the first half fraction, 76.7 mg of (3R,4R)-3-azidomethyl-1-benzyl-4-fluoropyrrolidine was obtained as a pale brown oil.

MS ($EI^+$):m/z=234 ($M^+$).

HRMS ($EI^+$): Calcd for $C_{12}H_{15}FN_4$: 234.1281; found: 234.1263.

From the second half fraction, 220 mg of (3R,4S)-3-azidomethyl-1-benzyl-4-fluoropyrrolidine was obtained as a pale brown oil.

MS (EI⁺): m/z=234 (M⁺).

HRMS (EI⁺): Calcd for $C_{12}H_{15}FN_4$: 234.1281; found: 234.1269.

Step 5:

(3R,4S)-3-Azidomethyl-1-benzyl-4-fluoropyrrolidine (215 mg) was dissolved in ethanol (3 mL). To this solution, platinum oxide (IV) (30.0 mg) was added and the mixture was stirred at room temperature for 5 hours in a stream of hydrogen (provided from a balloon). Subsequently, the catalyst was removed from the reaction mixture by filtration through a Celite pad. The removed catalyst and the Celite pad were washed with ethanol. The filtrate and the washing solution were combined and the combined organic layer was concentrated under reduced pressure to obtain 191 mg of (3S,4S)-3-aminomethyl-1-benzyl-4-fluoropyrrolidine as a brown oil.

MS (CI⁺): m/z=209 (MH⁺).

HRMS (CI⁺): Calcd for $C_{12}H_{18}FN_2$: 209.1454; found: 209.1465.

Step 6:

(3S,4S)-3-Aminomethyl-1-benzyl-4-fluoropyrrolidine (186 mg) was dissolved in methanol (4 mL). To this solution, molecular sieves 4A (80.0 mg) and benzaldehyde (90.8 µL) were sequentially added and the mixture was stirred at room temperature for 1 hour. Subsequently, a borane-pyridine complex (90.2 µL) was added and the mixture was further stirred at room temperature for 3 hours. This was followed by addition of 6 mol/L hydrochloric acid (1.5 mL) and stirring for 1 hour. Subsequently, a 6 mol/L aqueous solution of sodium hydroxide was added to make the mixture basic and the mixture was extracted with diethyl ether (3×10 mL). The diethyl ether extracts were combined and the combined diethyl ether layer was dried over anhydrous sodium sulfate and was then concentrated under reduced pressure. The resulting residue was purified on a silica gel column (eluant=hexane:ethyl acetate=4:1) to give 179 mg of (3S,4S)-1-benzyl-3-benzylaminomethyl-4-fluoropyrrolidine as a pale brown oil.

MS (CI⁺): m/z=299 (MH⁺).

HRMS (CI⁺): Calcd for $C_{19}H_{24}FN_2$: 299.1924; found: 299.1960.

Step 7:

(3S,4S)-1-Benzyl-3-benzylaminomethyl-4-fluoropyrrolidine (175 mg) was dissolved in methanol (2 mL). To this solution, molecular sieves 3A (180 mg), acetic acid (0.36 mL), [(1-ethoxycyclopropyl)oxy]trimethylsilane (0.47 mL) and sodium cyanoborohydride (110 mg) were added and the mixture was heat-refluxed for 3 hours while being stirred. Subsequently, insoluble materials were removed from the reaction mixture by filtration through a Celite pad. The insoluble materials and the Celite pad were washed with methanol. The filtrate and the washing solution were combined and a 2mol/L aqueous solution of sodium hydroxide was added to make the combined organic layer basic (pH14). Methanol was then removed under reduced pressure and the residue was extracted with diethyl ether (3×100 mL). The diethyl ether extracts were combined and the combined diethyl ether layer was dried over anhydrous sodium sulfate and was then concentrated under reduced pressure. The resulting residue was purified on a silica gel column (eluant=hexane:ethyl acetate=4:1) to give 172 mg of (3R,4S)-3-(N-benzyl-N-cyclopropyl)aminomethyl-1-benzyl-4-fluoropyrrolidine as a colorless tar-like product.

MS (CI⁺): m/z=339 (MH⁺).

HRMS (CI⁺): Calcd for $C_{22}H_{28}FN_2$: 339.2237; found: 339.2285.

Step 8:

(3R,4S)-3-(N-Benzyl-N-cyclopropyl)aminomethyl-1-benzyl-4-fluoropyrrolidine (170 mg) was dissolved in ethanol (10 mL). To this solution, 10% palladium carbon (200 mg) and chloroform (0.17 mL) were added and the mixture was stirred at 50° C. for 23 hours under a hydrogen pressure of $3.9 \times 10^5$ Pa. Subsequently, palladium carbon was removed from the reaction mixture by filtration through a Celite pad. The removed palladium carbon and the Celite pad were washed with ethanol. The filtrate and the washing solution were then combined and the combined organic layer was concentrated under reduced pressure. To the resulting residue, a 30% aqueous solution of sodium hydroxide (approximately 1 mL) was added. Subsequently, sodium chloride was added to saturation and the mixture was extracted with diethyl ether (3×10 mL). The diethyl ether extracts were combined and the combined diethyl ether layer was dried over anhydrous sodium sulfate and was then concentrated under reduced pressure to give 65.4 mg of (3R,4S)-3-cyclopropylaminomethyl-4-fluoropyrrolidine as a pale brown oil. This compound was identical to the compound obtained in Reference Example 11 (Process (I)).

Reference Example 13

Synthesis of (3R,4R)-3-cyclopropylaminomethyl-4-fluoropyrrolidine

Step 1:

(3R,4R)-[1-Benzyloxycarbonyl-4-hydroxypyrrolidin-3-yl]methanol (2.50 g), triphenylphosphine (5.74 g), and benzoic acid (2.55 g) were dissolved in tetrahydrofuran (60 mL). While this solution was cooled on a sodium chloride/ice bath, azodicarboxylic acid diethyl ester (40% toluene solution, 9.53 mL) was added dropwise. The mixture was stirred for 1 hour at 0° C. or below and then for additional 2 hours at room temperature and was subsequently concentrated under reduced pressure. The resulting residue was purified on a silica gel column (eluant=hexane:ethyl acetate=2:1). The eluted pale brown tar-like material was dissolved in ethanol (60 mL). To this solution, potassium carbonate (4.07 g) dissolved in water (30 mL) was added and the mixture was heat-refluxed for 3 hours while being stirred. Subsequently, the reaction mixture was concentrated under reduced pressure, and the resulting residue was dissolved in dichloromethane (200 mL). The dichloromethane solution was washed with a saturated aqueous solution of sodium chloride (2×50 mL), was dried over anhydrous sodium sulfate, and was then concentrated under reduced pressure. The resulting residue was purified on a silica gel column (eluant=ethyl acetate: methanol=10:1) to give 2.04 g of (3R,4S)-[1-benzyloxycarbonyl-4-hydroxypyrrolidin-3-yl]methanol as a milky white syrup-like product.

MS (EI) m/z=251 (M⁺).

Step 2:

(3R,4S)-[1-Benzyloxycarbonyl-4-hydroxypyrrolidin-3-yl]methanol (2.33 g), sodium azide (1.81 g), triphenylphosphine (2.67 g), and N,N-dimethylformamide (46 mL) were mixed with one another. While this mixture was cooled on an ice bath, a dichloromethane solution (10 mL) of carbon tetrabromide (3.38 g) was added dropwise. The reaction mixture was stirred for 13 hours at room temperature and additional 3 hours at 60° C., followed by addition of methanol (3 mL) and concentration under reduced pressure. The resulting residue was dissolved in ethyl acetate (200 mL) and was washed with a saturated aqueous solution of sodium chloride (2×50 mL), followed by drying over anhydrous sodium sulfate and concentration under reduce pressure. The resulting residue was purified on a silica gel column (eluant=ethyl acetate:hexane=2:1) to give 2.18 g of (3R,4S)-3-azidomethyl-1-benzyloxycarbonyl-4-hydroxypyrrolidine as a milky white syrup-like product.

MS (FAB$^+$): m/z=277 (MH$^+$).

Step 3:

(3R,4S)-3-Azidomethyl-1-benzyloxycarbonyl-4-hydroxypyrrolidine (300 mg) was dissolved in dichloromethane (6 mL). While this solution was cooled on an ice bath, diethylaminosulfur trifluoride (0.43 mL) was added dropwise. The mixture was stirred at room temperature for 4 hours. While the reaction vessel was cooled on an ice bath, a saturated aqueous solution of sodium hydrogen carbonate (6 mL) was added and the dichloromethane layer was collected. The collected dichloromethane layer was washed with a saturated aqueous solution of sodium chloride (2×2 mL), was dried over anhydrous sodium sulfate, and was then concentrated under reduced pressure. The resulting residue was purified on a silica gel column (eluant=hexane:ethyl acetate=2:1) to give 211 mg of a mixture of (3R,4R)-3-azidomethyl-1-benzyloxycarbonyl-4-fluoropyrrolidine and 3-azidomethyl-1-benzyloxycarbonyl-3-pyrroline.

Step 4:

Platinum oxide (IV) (50.0 mg) was suspended in ethanol (7 mL) and the suspension was stirred at room temperature for 30 min in a stream of hydrogen (provided from a balloon). To this suspension, an ethanol solution (3 mL) of a mixture (551 mg) of (3R,4R)-3-azidomethyl-1-benzyloxycarbonyl-4-fluoropyrrolidine and 3-azidomethyl-1-benzyloxycarbonyl-3-pyrroline was added, and the mixture was stirred at room temperature for 5 hours in a stream of hydrogen (provided from a balloon). Subsequently, the catalyst was removed from the reaction mixture by filtration and was washed with ethanol. The filtrate and the washing solution were combined and the combined organic layer was concentrated under reduced pressure. The resulting residue was then purified on a silica gel column (eluant=ethyl acetate shifted to ethyl acetate: methanol=10:1) to give 313 mg of a mixture of (3S,4R)-3-aminomethyl-1-benzyloxycarbonyl-4-fluoropyrrolidine and 3-aminomethyl-1-benzyloxycarbonyl-3-pyrroline.

Step 5:

A mixture (310 mg) of (3S,4R)-3-aminomethyl-1-benzyloxycarbonyl-4-fluoropyrrolidine and 3-aminomethyl-1-benzyloxycarbonyl-3-pyrroline was dissolved in methanol (4 mL). To this solution, molecular sieves 4A (130 mg) and benzaldehyde (0.13 mL) were sequentially added and the mixture was stirred at room temperature for 1 hour. Subsequently, a borane-pyridine complex (0.19 mL) was added and the mixture was further stirred at room temperature for 4 hours. This was followed by addition of 6 mol/L hydrochloric acid (2 mL) and stirring at room temperature for 1 hour. Subsequently, a 30% aqueous solution of sodium hydroxide was added to make the mixture basic and the mixture was extracted with diethyl ether (3×10 mL). The diethyl ether extracts were combined and the combined diethyl ether layer was concentrated under reduced pressure.

The resulting residue was purified on a silica gel column (eluant=dichloromethane: methanol=10:1) to give 177 mg of (3S,4R)-3-benzylaminomethyl-1-benzyloxycarbonyl-4-fluoropyrrolidine as a pale yellow oil.

MS (FAB$^+$): m/z=343 (MH$^+$).

HRMS (FAB$^+$): Calcd for $C_{20}H_{24}FN_2O_2$: 343.1822; found: 343.1815.

Step 6:

(3S,4R)-3-Benzylaminomethyl-1-benzyloxycarbonyl-4-fluoropyrrolidine (170 mg) was dissolved in methanol (5 mL). To this solution, molecular sieves 3A (160 mg), acetic acid (0.29 mL), [(1-ethoxycyclopropyl)oxy]trimethylsilane (0.40 mL), and sodium cyanoborohydride (93.5 mg) were added and the mixture was heat-refluxed for 3 hours while being stirred. Subsequently, insoluble materials were removed from the reaction mixture by filtration through a Celite pad. The insoluble materials and the Celite pad were washed with methanol. The filtrate and the washing solution were combined and a 2mol/L aqueous solution of sodium hydroxide was added to make the combined organic layer basic (pH>12). Methanol was then removed under reduced pressure and the residue was extracted with diethyl ether (3×10 mL). The diethyl ether extracts were combined and the combined diethyl ether layer was dried over anhydrous sodium sulfate and was then concentrated under reduced pressure. The resulting residue was purified on a silica gel column (eluant=hexane:ethyl acetate=2:1) to give 166 mg of (3S,4R)-3-(N-benzyl-N-cyclopropyl)aminomethyl-1-benzyloxycarbonyl-4-fluoropyrrolidine as a colorless tar-like product.

MS (FAB$^+$): m/z=383 (MH$^+$).

HRMS (FAB$^+$): Calcd for $C_{23}H_{28}FN_2O_2$: 383.2135; found: 383.2119.

Step 7:

(3S,4R)-3-(N-Benzyl-N-cyclopropyl)aminomethyl-1-benzyloxycarbonyl-4-fluoropyrrolidine (160 mg) was dissolved in ethanol (3 mL). To this solution, 10% palladium carbon (20.0 mg) was added and the mixture was stirred at room temperature for hours in a stream of hydrogen (provided from a balloon). Subsequently, the catalyst was collected from the reaction mixture by filtration through a Celite pad. The collected catalyst and the Celite pad were washed with ethanol. The filtrate and the washing solution were combined and the resulting residue was purified on a silica gel column (eluant=ethyl acetate: methanol=20:1, shifted to dichloromethane: methanol=10:1) to give 50.7 mg of (3R,4R)-3-cyclopropylaminomethyl-4-fluoropyrrolidine as a colorless oil.

MS (FAB$^+$): m/z=159 (MH$^+$).

HRMS (FAB$^+$): Calcd for $C_8H_{16}FN_2$: 159.1298; found: 159.1286.

Reference Example 14

Synthesis of (3R,4S)-3-[(N-tert-butoxycarbonyl-N-cyclopropyl)amino]methyl-4-fluoromethylpyrrolidine Step 1:

(1S,5R)-7-[(1R)-1-Phenylethyl]-3-oxa-7-azabicyclo[3.3.0]octane-2-one (7.73 g, 33.4 mmol) was dissolved in ethanol (92 mL). To this solution, cyclopropylamine (46.3 ml) was added, and the mixture was stirred at 80° C. for 44 hours and was subsequently concentrated under reduced pressure. The resulting residue was dissolved in ethyl acetate (300 mL) and the solution was washed with water (2×50 mL), followed by drying over anhydrous sodium sulfate and concentration under reduced pressure. To the resulting residue, diisopropyl ether (300 mL) was added and the mixture was heated to form crystal and was then concentrated to approximately ½. The formed crystal was collected by filtration and the collected crystal was washed with diisopropyl ether and was dried under reduced pressure to give 4.41 g of (3R,4S)-N-cyclopropyl-4-hydroxymethyl-1-[(1S)-1-phenylethyl]pyrrolidine-3-carboxamide as a white crystal. The filtrate and the washing solution were combined and the combined solvent was concentrated under reduced pressure. The resulting residue was purified on a silica gel column (eluant=hexane:ethyl acetate=1:1, shifted to ethyl acetate) to obtain additional 1.50 g of (3R,4S)-N-cyclopropyl-4-hydroxymethyl-1-[(1S)-1-phenylethyl]pyrrolidine-3-carboxamide. The total amount of the compound was 5.91 g.

MS (EI) m/z=288 (M$^+$).

Elementary analysis (%): Calcd for $C_{17}H_{24}N_2O_2 \cdot 0.2H_2O$: C, 69.93, H 8.42, N, 9.59; found: C, 70.16, H, 8.32, N, 9.60.

Step 2:

(3R,4S)-N-Cyclopropyl-4-hydroxymethyl-1-[(1S)-1-phenylethyl]pyrrolidine-3-carboxamide (7.54 g) was dissolved in N,N-dimethylformamide (180 mL). While this solution was cooled on an ice bath, imidazole (2.67 g) and tert-butylchlorodimethylsilane (4.72 g) were sequentially added. The mixture was stirred at room temperature for 90 min and was subsequently concentrated under reduced pressure. The resulting residue was dissolved in ethyl acetate (300 mL) and the solution was washed with water (2×100 mL), followed by drying over anhydrous sodium sulfate and concentration under reduced pressure. The resulting residue was purified on a silica gel column (eluant=ethyl acetate) to give 7.05 g of (3R,4S)-N-cyclopropyl-4-(tert-butyldimethylsilyl)oxymethyl-1-[(1S)-1-phenylethyl]pyrrolidine-3-carboxamide as a pale yellow tar-like product.

MS (EI) m/z: =402 (M$^+$).

Step 3:

(3R,4S)-N-Cyclopropyl-4-(tert-butyldimethylsilyl)oxymethyl-1-[(1S)-1-phenylethyl]pyrrolidine-3-carboxamide (7.00 g) was dissolved in toluene (70 mL). To this solution, borane-dimethyl sulfide complex (2.20 mL) was added and the mixture was heat-refluxed for 5 hours while being stirred. Subsequently, the reaction mixture was allowed to cool to room temperature. Following addition of a 10% aqueous solution of sodium carbonate (42 mL), the mixture was stirred at 100° C. for 1 hour and the toluene layer was separated. The toluene layer was washed with water (2×30 mL), was dried over anhydrous sodium sulfate, and was then concentrated under reduced pressure. The resulting residue was purified on a silica gel column (eluant=hexane:ethyl acetate=4:1) to give 4.78 g of (3S,4S)-4-(tert-butyldimethylsilyl)oxymethyl-3-cyclopropylaminomethyl-1-[(1S)-1-phenylethyl]pyrrolidine as a colorless oil.

Step 4:

(3S,4S)-4-(tert-Butyldimethylsilyl)oxymethyl-3-cyclopropylaminomethyl-1-[(1S)-1-phenylethyl]pyrrolidine (4.70 g) was dissolved in dichloromethane (70 mL). To this solution, di-tert-butyldicarbonate (2.77 g) was added and the mixture was stirred at room temperature for 2 hours. Subsequently, the reaction mixture was concentrated under reduced pressure and the resulting residue was purified on a silica gel column (eluant=hexane:ethyl acetate=4:1, shifted to 1:1) to give 5.28 g of (3R,4S)-3-[(N-tert-butoxycarbonyl-N-cyclopropyl)amino]methyl-4-(tert-butyldimethylsilyl)oxymethyl-1-[(1S)-1-phenylethyl]pyrrolidine as a colorless oil.

Step 5:

Process (A): (3R,4S)-N-Cyclopropyl-4-hydroxymethyl-1-[(1S)-1-phenylethyl]pyrrolidine-3-carboxamide (1.49 g) was dissolved in toluene (15 mL). To this solution, a borane-dimethyl sulfide complex (0.65 mL) was added and the mixture was heat-refluxed for 6 hours while being stirred. Subsequently, the reaction mixture was allowed to cool to room temperature. Following addition of a 10% aqueous solution of sodium carbonate (12.4 mL), the mixture was stirred at 100° C. for 1 hour and the toluene layer was separated. The toluene layer was then washed with water (10 mL) and was dried over anhydrous sodium sulfate. Following addition of di-tert-butyldicarbonate (1.13 g), the mixture was stirred at room temperature for 30 min and was subsequently allowed to stand overnight. The reaction mixture was then concentrated under reduced pressure and the resulting residue was purified on a silica gel column (eluant=hexane:ethyl acetate=1:1) to give 1.50 g of (3R,4S)-3-[(N-tert-butoxycarbonyl-N-cyclopropyl)amino]methyl-4-hydroxymethyl-1-[(1S)-1-phenylethyl]pyrrolidine as pale brown crystal.

Process (B): (3R,4S)-3-[(N-tert-Butoxycarbonyl-N-cyclopropyl)amino]methyl-4-(tert-butyldimethylsilyl)oxymethyl-1-[(1S)-1-phenylethyl]pyrrolidine (3.02 g) was dissolved in tetrahydrofuran (45 mL). While this solution was cooled on an ice bath, tetrabutylammonium fluoride (1mol/L tetrahydrofuran solution, 7.42 ml) was added dropwise and the mixture was stirred at room temperature for 2 hours. Subsequently, a saturated aqueous solution of sodium chloride (60 mL) was added and the mixture was extracted with ethyl acetate (2×150 mL). The ethyl acetate extracts were combined and the combined ethyl acetate layer was washed with a saturated aqueous solution of sodium chloride (2×100 mL), followed by drying over anhydrous sodium sulfate and concentration under reduced pressure. The resulting residue was dissolved in ethyl acetate (10 mL) and the formed crystal was collected by filtration, was washed with a small amount of ethyl acetate, and was then dried under reduced pressure to give 781 mg of (3R,4S)-3-[(N-tert-butoxycarbonyl-N-cyclopropyl)amino]methyl-4-hydroxymethyl-1-[(1S)-1-phenylethyl]pyrrolidine as a white crystal. The filtrate and the washing solution were combined and the combined organic layer was concentrated under reduced pressure. The resulting residue was purified on a silica gel column (eluant=hexane:ethyl acetate=1:1) to give additional 1.43 g of (3R,4S)-3-[(N-tert-butoxycarbonyl-N-cyclopropyl)amino]methyl-4-hydroxymethyl-1-[(1S)-1-phenylethyl]pyrrolidine. The total amount of the compound was 2.21 g.

MS (EI) m/z: =374 (M$^+$).

Elementary analysis (%): Calcd for $C_{22}H_{34}N_2O_3$: C, 70.55; H, 9.15; N, 7.48; found: C, 70.56, H, 9.29, N, 7.52.

Step 6:

(3R,4S)-3-[(N-tert-Butoxycarbonyl-N-cyclopropyl)amino]methyl-4-hydroxymethyl-1-[(1S)-1-phenylethyl]pyrrolidine (2.66 g) was dissolved in dichloromethane (40 mL). While this solution was cooled on a sodium chloride/ice bath, triethylamine (1.05 mL) was added. This was followed by dropwise addition of methanesulfonyl chloride (0.58 mL). After being stirred at −5° C. for 30 min, the reaction mixture was washed with water, was dried over anhydrous sodium sulfate, and was then concentrated under reduced pressure. The resulting residue was dissolved in tetrahydrofuran (21 mL). To this solution, tetrabutylammonium fluoride (1mol/L tetrahydrofuran solution, 21.3 mL) was added and the mixture was heat-refluxed for 2 hours while being stirred. The reaction mixture was concentrated under reduced pressure and the resulting residue was dissolved in ethyl acetate (200 mL). The ethyl acetate solution was washed with water (2×50 mL), was dried over anhydrous sodium sulfate, and was then concentrated under reduced pressure. The resulting residue was purified on a silica gel column (eluant=hexane:ethyl acetate=4:1, shifted to 1:1) to give 1.13 g of (3R,4S)-3-[(N-tert-butoxycarbonyl-N-cyclopropyl)amino]methyl-4-fluoromethyl-1-[(1S)-1-phenylethyl]pyrrolidine as a pale brown tar-like product.

MS (EI) m/z=376 (M+).

Step 7:

(3R,4S)-3-[(N-tert-Butoxycarbonyl-N-cyclopropyl) amino]methyl-4-fluoromethyl-1-[(1S)-1-phenylethyl]pyrrolidine (1.10 g) was dissolved in methanol (20 mL). To this solution, a suspension of 10% palladium carbon (230 mg) in water (4 mL) and ammonium formate (921 mg) were sequentially added and the mixture was heat-refluxed for 90 min while being stirred. Subsequently, the catalyst was removed from the reaction mixture by filtration through a Celite pad. The removed catalyst and the Celite pad were washed with ethanol containing 20% water. The filtrate and the washing solution were combined and the combined solution was concentrated under reduced pressure. Water (20 mL) was then added to the resulting residue. While this mixture was cooled on an ice bath, a 30% aqueous solution of sodium hydroxide was added to make the mixture basic (pH14). The mixture was subsequently extracted with dichloromethane (50 mL×2). The dichloromethane extracts were combined washed with water (2×20 mL), and the combined dichloromethane layer was dried over anhydrous sodium sulfate and was then concentrated under reduced pressure. The resulting residue was purified on a silica gel column (eluant=dichloromethane: methanol=20:1) to give 684 mg of (3R,4S)-3-[(N-tert-butoxycarbonyl-N-cyclopropyl)amino]methyl-4-fluoromethylpyrrolidine as a pale brown tar-like product.

MS (EI) m/z=272 (M+).

Reference Example 15

Synthesis of (3R,4R)-3-cyclopropylaminomethyl-4-methylpyrrolidine•trifluoroacetate Step 1:

1-Benzyl-4-(R)-methyl-3-(R)-[(4-(S)-phenyl-2-oxazolidinone-3-yl)carbonyl]pyrrolidine (150 g) was dissolved in cyclopropylamine (650 mL). The mixture was stirred at room temperature for 23 hours and was subsequently concentrated under reduced pressure. To the resulting residue, diisopropyl ether (800 mL) was added and the mixture was stirred at room temperature for 70 min. The resulting crystal was then collected by filtration. The collected crystal was then dissolved in dichloromethane (800 mL) and the solution was extracted with 1mol/L hydrochloric acid (2×400 mL). The 1 mol/L hydrochloric acid extracts were combined. While the combined solution was cooled on an ice bath, a 30% aqueous solution of sodium hydroxide was added to make the solution basic (pH13). The resulting crystal was collected by filtration, was sequentially washed with water and diisopropyl ether, and was then dried under reduced pressure to give 52.2 g of (3R,4R)-1-1-benzyl-N-cyclopropyl-4-methyl-3-pyrrolidinecarboxamide as a white crystal.

Step 2:

(3R,4R)-1-Benzyl-N-cyclopropyl-4-methyl-3-pyrrolidinecarboxamide (70.0 g) was dissolved in toluene (700 mL). While this solution was cooled on an ice bath, a borane-dimethyl sulfide complex (90%, 34.3 mL) was added dropwise. The mixture was then stirred for 15 min and was heat-refluxed. After the reaction mixture was cooled to room temperature, a 10% aqueous solution of $Na_2CO_3$ (400 mL) was added and the mixture was stirred at 100° C. for 2 hours. The mixture was cooled to room temperature and the toluene layer was separated. The toluene layer was then washed with water (2×250 mL), was dried over anhydrous sodium sulfate, and was concentrated under reduced pressure. The resulting residue was purified by distillation under reduced pressure to obtain (3S,4R)-1-benzyl-3-cyclopropylaminomethyl-4-methylpyrrolidine (62.1 g) as a colorless oil.

Step 3:

(3S,4R)-1-Benzyl-3-cyclopropylaminomethyl-4-methylpyrrolidine (25.0 g) was dissolved in ethanol (200 mL). To this solution, trifluoroacetic acid (15.7 mL) and 10% palladium carbon (12.5 g) were added and the mixture was stirred at room temperature for 9 hours under a hydrogen pressure of $3.9×10^5$ Pa. The catalyst was collected from the reaction mixture by filtration and was washed with ethanol containing 25% water (300 mL). The filtrate and the washing solution were combined and the combined solution was concentrated under reduced pressure. The resultant pale brown crystal was suspended in tetrahydrofuran (100 mL) and was collected by filtration. The collected crystal was washed with tetrahydrofuran and was dried under reduced pressure to give 34.1 g of (3R,4R)-3-cyclopropylaminomethyl-4-methylpyrrolidine-trifluoroacetate as a white crystal.

Example 1

Synthesis of (3R)-10-[(3S)-3-cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid Process (A): [(3R)-9,10-Difluoro-3-fluoromethyl-2,3-dihydro-7-oxo-7H-pyrido[1,2,3-d,e][1,4]benzoxazine-6-carboxylato-$O^6,O^7$]difluoroboron (51.0 g), 3(R)-cyclopropylaminomethylpyrrolidine (24.7 g), triethylamine (24.6 mL) and dimethylsulfoxide (500 mL) were mixed with one another and the mixture was stirred at 70° C. for 1 hour. Subsequently, the reaction mixture was concentrated under reduced pressure and the resulting residue was purified on a silica gel column (eluant=dichloromethane: methanol=10: 1). The eluates were combined and the combined solution was concentrated under reduced pressure. To the resulting residue, 80% ethanol (2500 mL) and triethylamine (25.0 mL) were added and the mixture was heat-refluxed for 2 hours while being stirred. Subsequently, the reaction mixture was left on an ice bath for 2 hours and the resulting crystal was collected by filtration. The collected crystal was washed with ethanol, was suspended in purified water (300 ml), and was then collected by filtration. The collected crystal was dried under reduced pressure and was purified on a silica gel column (eluant=dichloromethane: methanol=10:1). The eluates were combined and the combined solution was concentrated under reduced pressure. The resulting residue was dissolved in ethanol (2000 mL) by heating and the solution was allowed to stand for 14 hours at room temperature. The resultant crystal was collected by filtration and the collected crystal was washed with ethanol and was dried under reduced pressure to give 27.7 g of (3 R)-10-[(3 S)-3-cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid as a yellow powder.

Process B: To a dichloromethane solution (273 mL) of bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (22.6 g), (3R)-3-cyclopropylaminomethylpyrrolidine (8.41 g) and triethylamine (7.59 g) were added and the mixture was allowed to stand at room temperature for 13 hours. Subsequently, the reaction mixture was sequentially washed with water (200 mL) and a saturated aqueous solution of sodium chloride (50 ml), was dried over anhydrous sodium sulfate, and was then concentrated under reduced pressure. The resulting residue was purified on a silica gel column (dichloromethane: methanol=15:1) to obtain a yellow amorphous product. To this product, a 5% aqueous solution of acetic acid (100 mL) was added and the mixture was stirred at 80° C. for 3 hours. Subsequently, the reaction mixture was washed with ethyl acetate (100 mL). While the mixture was cooled on an ice bath, a 1 mol/L aqueous solution of sodium hydroxide was added to adjust the pH to 7.01 and the mixture was further stirred for 0.5 hours. The resultant crystal was collected by filtration, washed with purified water (2×50 mL), and was then dissolved in ethanol (1200 mL) by heating. The solution was allowed to stand at room temperature for 12 hours. Subsequently, the resulting crystal was collected by filtration, followed by washing with ethanol and drying under reduced pressure, to give 11.2 g of (3R)-10-[(3S)-3-cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid as a yellow crystal.

MS (EI) m/z: 419 ($M^+$).

Elementary analysis (%): Calcd for $C_{21}H_{23}F_2N_3O_4$: C, 60.14; H, 5.53; N, 10.02; found: C, 60.01; H, 5.47; N, 9.94.

Example 2

Synthesis of (3R)-10-[(3R)-3-cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (982 mg) was reacted with (3S)-3-cyclopropylaminomethylpyrrolidine (335 mg) to give 587 mg of (3R)-10-[(3R)-3-cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid as a yellow crystal.

MS ($FAB^+$) m/z: 420 ($MH^+$).

Elementary analysis (%): Calcd for $C_{21}H_{23}F_2N_3O_4 \cdot 0.25H_2O$: C, 59.50; H, 5.59, N, 9.91; found: C, 59.68; H, 5.47; N, 9.97.

Example 3

Synthesis of (3R)-10-[3-cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (513 mg) was reacted with 3-cyclopropylaminomethylpyrrolidine (185 mg) to give 231 mg of (3R)-10-(3-cyclopropylaminomethyl-1-pyrrolidinyl)-9-fluoro-3-fluoromethyl-2,3-dihydro-7-oxo-7H-pyrido[1,2,3-d,e][1,4]benzoxazine-6-carboxylic acid as a yellow crystal.

MS ($FAB^+$) m/z: 420 ($MH^+$).

Elementary analysis (%): Calcd for $C_{21}H_{23}F_2N_3O_4 \cdot 0.25H_2O$: C, 59.50, H, 5.59, N, 9.91; found: C, 59.41, H, 5.41, N, 9.89.

Example 4

Synthesis of (3S)-10-[(3S)-3-cyclopropylaminomethyl-1-pyrrolidinyl]-9-fluoro-2,3-dihydro-3-methoxymethyl-1-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methoxymethyl-7-oxo-7H-pyrido[1,2,3-d,e][1,4]benzoxazine-6-carboxylato-$O^6,O^7$]boron (790 mg) was reacted with (3R)-3-cyclopropylaminomethylpyrrolidine (303 mg) to give 602 mg of (3S)-10-[(3S)-3-cyclopropylaminomethyl-1-pyrrolidinyl]-9-fluoro-2,3-dihydro-3-methoxymethyl-7-oxo-7H-pyrido[1,2,3-d,e][1,4]benzoxazine-6-carboxylic acid as a yellow crystal.

MS ($FAB^+$) m/z: 432 ($MH^+$).

Elementary analysis (%): Calcd for $C_{22}H_{26}FN_3O_5$: C, 61.24; H, 6.07; N, 9.74; found: C, 61.01, H, 6.04, N, 9.73.

Example 5

Synthesis of (3S)-3-acetoxymethyl-10-[(3S)-3-cyclopropylaminomethyl-1-pyrrolidinyl]-9-fluoro-2,3-dihydro-7-oxo-7H-pyrido[1,2,3-d,e][1,4]benzoxazine-6-carboxylic acid In a similar manner to Process (B) in Example 1, bis(acetato-O)[(3S)-3-acetoxymethyl-9,10-difluoro-2,3-dihydro-7-oxo-7H-pyrido[1,2,3-d,e][1,4]benzoxazine-6-carboxylato-$O^6,O^7$]boron (934 mg) was reacted with (3R)-3-cyclopropylaminomethylpyrrolidine (337 mg) to give 612 mg of (3S)-3-acetoxymethyl-10-[(3S)-3-cyclopropylaminomethyl-1-pyrrolidinyl]-9-fluoro-2,3-dihydro-7-oxo-7H-pyrido[1,2,3-d,e][1,4]benzoxazine-6-carboxylic acid as a yellow crystal.

MS ($FAB^+$) m/z: 460 ($MH^+$).

Elementary analysis (%): Calcd for $C_{23}H_{26}FN_3O_6 \cdot H_2O$: C, 57.85, H 5.91, N, 8.80; found: C, 57.94, H, 5.83, N, 8.89.

Example 6

Synthesis of (3S)-10-[(3S)-3-cyclopropylaminomethyl-1-pyrrolidinyl]-9-fluoro-2,3-dihydro-3-hydroxymethyl-7-oxo-7H-pyrido[1,2,3-d,e][1,4]benzoxazine-6-carboxylic acid A 1 mol/L aqueous solution of sodium hydroxide (8.0 mL) containing (3S)-3-acetoxymethyl10-[(3S)-3-cyclopropylaminomethyl-1-pyrrolidinyl]-9-fluoro-2,3-dihydro-7-oxo-7H-pyrido[1,2,3-d,e][1,4]benzoxazine-6-carboxylic acid (368 mg) was stirred at 50° C. for 2 hours. While this mixture was cooled on an ice bath, 1mol/L hydrochloric acid was added to adjust the pH to 7.05 and the mixture was further stirred for 0.5 hours. The resultant crystal was collected by filtration, was washed with purified water, and was then dissolved in ethanol (50 mL) by heating. The solution was allowed to stand at room temperature for 2 hours. Subsequently, the resulting crystal was collected by filtration, was washed ethanol, and was then dried under reduced pressure to give 251 mg of (3S)-10-[(3S)-3-cyclopropylaminomethyl-1-pyrrolidinyl]-9-fluoro-2,3-dihydro-3-hydroxymethyl-7-oxo-7H-pyrido[1,2,3-d,e][1,4]benzoxazine-6-carboxylic acid as a yellow crystal.

MS (FAB$^+$) m/z: 418 (MH$^+$).

Elementary analysis (%): Calcd for $C_{21}H_{24}FN_3O_5 \cdot 0.5H_2O$: C, 59.15, H 5.91, N, 9.85; found: C, 59.16, H, 5.92, N, 9.88.

Example 7

Synthesis of 10-[(3S)-3-cyclopropylaminomethyl-1-pyrrolidinyl]-9-fluoro-2,3-dihydro-3-methylene-7-oxo-7H-pyrido[1,2,3-d,e][1,4]benzoxazine-6-carboxylic acid (3R)-10-[(3S)-3-Cyclopropylaminomethyl-1-pyrrolidinyl]-9-fluoro-3-fluoromethyl-2,3-dihydro-7-oxo-7H-pyrido[1,2,3-d,e][1,4]benzoxazine-6-carboxylic acid (252 mg) was suspended in ethanol (1 mL). To this suspension, a 1 mol/L aqueous solution of sodium hydroxide (6 mL) was added and the mixture was stirred at room temperature for 2 hours. Subsequently, the reaction mixture was concentrated under reduced pressure and the resulting residue was dissolved in purified water (10 ml). While this solution was cooled on an ice bath, 1 mol/L hydrochloric acid was added to adjust the pH to 7.03 and the mixture was further stirred for 0.5 hours. The resultant crystal was collected by filtration to obtain 214 mg of 10-[(3S)-cyclopropylmethylamino-1-pyrrolidinyl]-9-fluoro-2,3-dihydro-3-methylene-7-oxo-7H-pyrido[1,2,3-d,e][1,4]benzoxazine-6-carboxylic acid as a yellow powder.

MS (FAB$^+$) m/z: 400 (MH$^+$).

Elementary analysis (%): Calcd for $C_{22}H_{23}FN_3O_4 \cdot 1.75H_2O$: C, 58.53; H, 5.96, N, 9.75; found: C, 58.62, H, 5.79, N, 9.76.

Example 8

Synthesis of (3R)-10-[(3S)-cyclopropylaminomethyl-1-pyrrolidinyl]-3-fluoromethyl-2,3-dihydro-7-oxo-7H-pyrido[1,2,3-d,e][1,4]benzoxazine-6-carboxylic acid In a similar manner to Process (B) in Example 1, bis(acetato-O)[(3R)-10-fluoro-3-fluoromethyl-2,3-dihydro-7-oxo-7H-pyrido[1,2,3-d,e][1,4]benzoxazine-6-carboxylato-O$^6$,O$^7$]boron (500 mg) was reacted with (3R)-3-cyclopropylaminomethylpyrrolidine (240 mg) to give 335 mg of (3R)-10-[(3S)-3-cyclopropylaminomethyl-1-pyrrolidinyl]-3-fluoromethyl-2,3-dihydro-7-oxo-7H-pyrido[1,2,3-d,e][1,4]benzoxazine-6-carboxylic acid as a yellow needle-shaped product.

MS (FAB$^+$) m/z: 402 (MH$^+$).

Elementary analysis (%): Calcd for $C_{21}H_{24}FN_3O_4$: C, 62.83; H, 6.03; N, 10.47; found: C, 62.56, H, 5.94, N, 10.40.

Example 9

Synthesis of (3S)-10-[(3S)-cyclopropylaminomethyl-1-pyrrolidinyl]-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-10-fluoro-2,3-dihydro-3-methyl-7-oxo-7H-pyrido[1,2,3-d,e][1,4]benzoxazine-6-carboxylato-O$^6$,O$^7$]boron (1000 mg) was reacted with (3R)-3-cyclopropylaminomethylpyrrolidine (431 mg) to give 335 mg of (3S)-10-[(3S)-3-cyclopropylaminomethyl-1-pyrrolidinyl]-2,3-dihydro-3-methyl-7-oxo-7H-pyrido[1,2,3-d,e][1,4]benzoxazine-6-carboxylic acid as a yellow needle-shaped product.

MS (EI$^+$) m/z: 383 (M$^+$).

Elementary analysis (%): Calcd for $C_{21}H_{25}N_3O_4$: C, 65.78; H, 6.57; N, 10.96; found: C, 65.58, H, 6.61, N, 10.91.

Example 10

Synthesis of (3S)-10-(trans-3-cyclopropylaminomethyl-4-methyl-1-pyrrolidinyl)-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-O$^6$,O$^7$]boron (300 mg) was reacted with trans-3-cyclopropylaminomethyl-4-methylpyrrolidine (136 mg) to give 166 mg of (3S)-10-(trans-3-cyclopropylaminomethyl-4-methyl-1-pyrrolidinyl)-9-fluoro-2,3-dihydro-3-methyl-7-oxo-7H-pyrido[1,2,3-d,e][1,4]benzoxazine-6-carboxylic acid as yellow crystal.

MS (EI$^+$) m/z: 415 (M$^+$).

Elementary analysis (%): Calcd for $C_{22}H_{26}FN_3O_4 \cdot 0.5H_2O$: C, 62.25, H 6.41, N, 9.90; found: C, 62.30, H, 6.17, N, 10.06.

Example 11

Synthesis of (3S)-10-[(3S,4R)-3-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-O$^6$,O$^7$]boron (500 mg) was reacted with (3R,4R)-3-cyclopropylamino-4-methylpyrrolidine (226 mg) to give 362 mg of (3S)-10-[(3S,4R)-3-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid as a yellow crystal.

MS (EI$^+$) m/z: 415 (M$^+$)

Elementary analysis (%): Calcd for $C_{22}H_{26}FN_3O_4$: C, 63.60; H, 6.31; N, 10.11; found: C, 63.41, H, 6.30, N, 10.17.

Example 12

Synthesis of (3S)-10-[(3R,4S)-3-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-$O^6,O^7$]boron (500 mg) was reacted with (3S,4S)-3-cyclopropylamino-4-methylpyrrolidine (226 mg) to give 276 mg of (3S)-10-[(3R,4S)-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid as a pale yellow crystal.

MS (EI$^+$) m/z: 415 (M$^+$).

Elementary analysis (%): Calcd for $C_{22}H_{26}FN_3O_4 \cdot 0.5H_2O$: C, 62.25; H, 6.41, N, 9.90; found: C, 62.23, H, 6.06, N, 9.92.

Example 13

Synthesis of (3S)-10-(cis-3-cyclopropylaminomethyl-4-methyl-1-pyrrolidinyl)-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-$O^6,O^7$]boron (220 mg) was reacted with cis-3-cyclopropylaminomethyl-4-methylpyrrolidine (100 mg) to give 109 mg of (3S)-10-(cis-3-cyclopropylaminomethyl-4-methyl-1-pyrrolidinyl)-9-fluoro-2,3-dihydro-3-methyl-7-oxo-7H-pyrido[1,2,3-d,e][1,4]benzoxazine-6-carboxylic acid as a yellow crystal.

MS (EI$^+$) m/z: 415 (M$^+$).

Elementary analysis (%): Calcd for $C_{22}H_{26}FN_3O_4 \cdot H_2O$: C, 60.96, H 6.51, N, 9.69; found: C, 61.27, H, 6.69, N, 9.52.

Example 14

Synthesis of (3S)-10-[(3S,4S)-3-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-$O^6,O^7$]boron (1000 mg) was reacted with (3R,4S)-cyclopropylamino-4-methylpyrrolidine (452 mg) to give 474 mg of (3S)-10-[(3S,4S)-3-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid as a yellow crystal.

MS (EI$^+$) m/z: 415 (M$^+$).

Elementary analysis (%): Calcd for $C_{22}H_{26}FN_3O_4 \cdot 0.25H_2O$: C, 62.92; H, 6.36, N, 10.01; found: C, 62.69, H, 6.52, N, 9.98.

Example 15

Synthesis of (3S)-10-[(3R,4R)-3-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-$O^6,O^7$]boron (250 mg) was reacted with (3S,4R)-3-cyclopropylamino-4-methylpyrrolidine (113 mg) to give 33 mg of (3S)-10-[(3R,4R)-cyclopropylaminomethyl-4-methyl-1-pyrrolidinyl]-9-fluoro-2,3-dihydro-3-methyl-7-oxo-7H-pyrido[1,2,3-d,e][1,4]benzoxazine-6-carboxylic acid as a pale yellow crystal.

MS (EI$^+$) m/z: 415 (M$^+$).

Elementary analysis (%): Calcd for $C_{22}H_{26}FN_3O_4 \cdot 0.5H_2O$: C, 62.25, H 6.41, N, 9.90; found: C, 61.98, H, 6.57, N, 9.91.

Example 16

Synthesis of (3R)-10-(trans-3-cyclopropylaminomethyl-4-methyl-1-pyrrolidinyl)-9-fluoro-3-fluoromethyl-2,3-dihydro-7-oxo-7H-pyrido[1,2,3-d,e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (300 mg) was reacted with trans-3-cyclopropylaminomethyl-4-methylpyrrolidine (130 mg) to give 110 mg of (3R)-10-(trans-3-cyclopropylaminomethyl-4-methyl-1-pyrrolidinyl)-9-fluoro-3-fluoromethyl-2,3-dihydro-7-oxo-7H-pyrido[1,2,3-d,e][1,4]benzoxazine-6-carboxylic acid.

MS (EI$^+$) m/z: 433 (M$^+$).

Elementary analysis (%): Calcd for $C_{22}H_{25}F_2N_3O_4$: C, 60.96; H, 5.81; N, 9.69; found: C, 60.81, H, 5.85, N, 9.66.

Example 17

Synthesis of (3R)-10-[(3S,4R)-3-cyclopropylaminomethyl-4-methyl-1-pyrrolidinyl]-9-fluoro-3-fluoromethyl-2,3-dihydro-7-oxo-7H-pyrido[1,2,3-d,e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (1000 mg) was reacted with (3R,4R)-cyclopropylamino-4-methylpyrrolidine (397 mg) to give 620 mg of (3R)-10-[(3S,4R)-3-cyclopropylaminomethyl-4-methyl-1-pyrrolidinyl]-9-fluoro-3-fluoromethyl-2,3-dihydro-7-oxo-7H-pyrido[1,2,3-d,e][1,4]benzoxazine-6-carboxylic acid as a yellow crystal.

MS (EI$^+$) m/z: 433 (M$^+$).

Elementary analysis (%): Calcd for $C_{22}H_{25}F_2N_3O_4$: C, 60.96; H, 5.81; N, 9.69; found: C, 60.81, H, 5.86, N, 9.63.

Example 18

Synthesis of (3R)-10-[(3S,4S)-3-cyclopropylaminomethyl-4-methyl-1-pyrrolidinyl]-9-fluoro-3-fluoromethyl-2,3-dihydro-7-oxo-7H-pyrido[1,2,3-d,e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (500 mg) was reacted with (3R,4R)-cyclopropylamino-4-methylpyrrolidine (199 mg) to give 422 mg of (3R)-10-[(3S,4S)-3-cyclopropylaminomethyl-4-methyl-1-pyrrolidinyl]-9-fluoro-3-fluoromethyl-2,3-dihydro-7-oxo-7H-pyrido[1,2,3-d,e][1,4]benzoxazine-6-carboxylic acid as a yellow crystal.

MS (EI$^+$) m/z: 433 (M$^+$).

Elementary analysis (%): Calcd for $C_{22}H_{25}F_2N_3O_4$: C, 60.96; H, 5.81; N, 9.69; found: C, 60.79, H, 5.91, N, 9.77.

Example 19

Synthesis of (3S)-10-(trans-3-cyclopropylaminomethyl-4-trifluoromethyl-1-pyrrolidinyl)-9-fluoro-2,3-dihydro-3-methyl-7-oxo-7H-pyrido[1,2,3-d,e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-$O^6,O^7$]boron (300 mg) was reacted with trans-3-cyclopropylaminomethyl-4-trifluoromethylpyrrolidine (198 mg) to give 87 mg of (3S)-10-(trans-3-cyclopropylaminomethyl-4-trifluoromethyl-1-pyrrolidinyl)-9-fluoro-2,3-dihydro-3-methyl-7-oxo-7H-pyrido[1,2,3-d,e][1,4]benzoxazine-6-carboxylic acid.

MS (FAB$^+$) m/z: 470 (MH$^+$).

Elementary analysis (%): Calcd for $C_{22}H_{23}F_4N_3O_4$: C, 56.29, H, 4.94, N, 8.95; found: C, 55.97, H, 4.84, N, 9.00.

Example 20

Synthesis of (3R)-10-[(3S,4S)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-$O^6,O^7$]boron (500 mg) was reacted with (3R,4S)-3-cyclopropylaminomethyl-4-fluoropyrrolidine (204 mg) to give 387 mg of (3R)-10-[(3S,4S)-3-cyclopropylaminomethyl-4-fluoro-1-pyrrolidinyl]-9-fluoro-3-fluoromethyl-2,3-dihydro-7-oxo-7H-pyrido[1,2,3-d,e][1,4]benzoxazine-6-carboxylic acid as a pale yellow crystal.

MS (FAB$^+$):m/z=438 (MH$^+$).

Elementary analysis (%): Calcd for $C_{21}H_{22}F_3N_3O_4$: C, 57.66; H, 5.07; N, 9.61, found: C, 57.47, H, 5.07, N, 9.57.

Example 21

Synthesis of (3S)-10-[(3S,4S)-3-cyclopropylamino-4-fluoro-1-pyrrolidinyl]-9-fluoro-2,3-dihydro-3-methyl-7-oxo-7H-pyrido[1,2,3-d.e][1,4]benzoxazine-6-carboxylic acid In a similar manner to Process (B) in Example 1, bis(acetato-O)[(3S)-9,10-difluoro-2,3-dihydro-3-methyl-7-oxo-7H-pyrido[1,2,3-d,e][1,4]benzoxazine-6-carboxylato-$O^6,O^7$]boron (64.6 mg) was reacted with (3R,4S)-3-cyclopropylaminomethyl-4-fluoropyrrolidine (25.0 mg) to give 18.5 mg of (3R)-10-[(3S,4S)-3-cyclopropylamino-4-fluoro-1-pyrrolidinyl]-9-fluoro-2,3-dihydro-3-methyl-7-oxo-7H-pyrido[1,2,3-d.e][1,4]benzoxazine-6-carboxylic acid as a yellow powder.

MS (FAB$^+$) m/z=420 (MH$^+$).

HRMS (FAB$^+$): Calcd for $C_{21}H_{24}F_2N_3O_4$: 420.1735; found: 420.1747.

Example 22

Synthesis of (3R)-10-[(3S,4S)-3-[(N-tert-butoxycarbonyl-N-cyclopropyl)amino]methyl-4-fluoromethyl-1-pyrrolidine]-9-fluoro-3-fluoromethyl-2,3-dihydro-7-oxo-7H-pyrido[1,2,3-d.e][1,4]benzoxazine-6-carboxylic acid Bis(acetato-O)[(3R)-9,10-difluoro-3-fluoromethyl-2,3-dihydro-7-oxo-7H-pyrido[1,2,3-d.e][1,4]benzoxazine-6-carboxylato-$O^6,O^7$]boron (912 mg), (3R,4S)-3-[(N-tert-butoxycarbonyl-N-cyclopropyl)amino]methyl-4-fluoromethylpyrrolidine (640 mg), triethylamine (0.33 mL) and acetonitrile (17 mL) were mixed with one another and the mixture was stirred at 60° C. for 90 min. Subsequently, the reaction mixture was concentrated under reduced pressure and the resulting residue was purified on a silica gel column (eluant=ethyl acetate: methanol=20:1). To the eluate, a 5% aqueous solution of acetic acid (17 mL) and ethanol (10 mL) were added and the mixture was stirred at 80° C. for 2 hours. The mixture was allowed to cool and the resulting crystal was collected by filtration, was washed with a mixture of water and ethanol, and was then dried under reduced pressure to give 915 mg of (3R)-10-[(3S,4S)-3-[(N-tert-butoxycarbonyl-N-cyclopropyl)amino]methyl-4-fluoromethyl-1-pyrrolidine]-9-fluoro-3-fluoromethyl-2,3-dihydro-7-oxo-7H-pyrido [1,2,3-d.e][1,4]benzoxazine-6-carboxylic acid as a yellow powder.

MS (EI) m/z=551 (M$^+$).

Elementary analysis (%): Calcd for $C_{27}H_{32}F_3N_3O_6 \cdot 0.5H_2O$: C, 57.85; H, 5.93, N, 7.50; found: C, 57.90, H, 5.80, N, 7.49.

Example 23

Synthesis of (3R)-10-[(3S,4S)-3-cyclopropyl]amino]methyl-4-fluoromethyl-1-pyrrolidinyl]-9-fluoro-3-fluoromethyl-2,3-dihydro-7-oxo-7H-pyrido[1,2,3-d.e][1,4]benzoxazine-6-carboxylic acid hydrochloride (3R)-10-[(3S,4S)-3-[(N-tert-Butoxycarbonyl-N-cyclopropyl)amino]methyl-4-fluoromethyl-1-pyrrolidine]-9- fluoro-3-fluoromethyl-2,3-dihydro-7-oxo-7H-pyrido[1,2,3-d.e][1,4]benzoxazine-6-carboxylic acid (860 mg) was dissolved in ethanol (9 mL) saturated with hydrogen chloride. The mixture was stirred at room temperature for 1 hour and was subsequently concentrated under reduced pressure. To the resulting residue, ethanol (50 mL) was added and the mixture was concentrated under reduced pressure. After repeating the ethanol addition and concentration once, ethanol (50 mL) was added to the resultant residue, and the mixture was heated to 70° C. and was then allowed to stand at room temperature for 1 hour. The resulting crystal was collected by filtration, followed by washing with ethanol and drying under reduced pressure, to give 762 mg of (3R)-10-[(3S,4S)-3-cyclopropyl]amino]methyl-4-fluoromethyl-1-pyrrolidinyl]-9-fluoro-3-fluoromethyl-2,3-dihydro-7-oxo-7H-pyrido[1,2,3-d.e][1,4]benzoxazine-6-carboxylic acid hydrochloride as a yellow crystal.

MS (FAB$^+$): m/z=452 (MH$^+$).

Elementary analysis (%): Calcd for $C_{22}H_{24}F_3N_3O_4 \cdot HCl \cdot H_2O \cdot 0.5C_2H_5OH$: C, 52.23, H, 5.72, N, 7.94; found: C, 52.17, H, 5.38, N, 8.20.

Example 24

Synthesis of (3R)-10-[(3S,4R)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid In a similar manner to Process (B) in Example 1, bis(acetato-O)[(3R)-9,10-difluoro-3-fluoromethyl-2,3-dihydro-7-oxo-7H-pyrido[1,2,3-d,e][1,4]benzoxazine-6-carboxylato-O$^6$,O$^7$]boron (100 mg) was reacted with (3R,4R)-3-cyclopropylaminomethyl-4-fluoropyrrolidine (40.6 mg) to give 71.0 mg of (3R)-10-[(3S,4R)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid as a pale yellow crystal.

MS (FAB$^+$): m/z=438 (MH$^+$).

Elementary analysis (%): Calcd for $C_{21}H_{22}F_3N_3O_4$: C, 57.66; H, 5.07; N, 9.61; found: C, 57.50, H, 5.18, N, 9.22.

Example 25

Synthesis of (3R)-10-[(3S,4S)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid methanesulfonate (3R)-10-[(3S,4S)-3-Cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid (50.0 mg) was suspended in ethanol (2 mL). To this suspension, methanesulfonic acid (15.0 μL) was added and the mixture was stirred at room temperature for 1 hour. The resulting crystal was collected by filtration, was washed with ethanol, and was then dried under reduced pressure to give 50.4 mg of (3R)-10-[(3S,4S)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid methanesulfonate as a pale yellow crystal.

MS (FAB$^+$): m/z=438 (MH$^+$).

Elementary analysis (%): Calcd for $C_{21}H_{22}F_3N_3O_4 \cdot CH_3SO_3H \cdot 0.25H_2O$: C, 49.11, H, 4.96, N, 7.81; found: C, 49.18, H, 4.86, N, 7.42.

Example 26

Synthesis of (3R)-10-[(3S,4S)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid hydrochloride (3R)-10-[(3S,4S)-3-Cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid (50.0 mg) was suspended in ethanol (2 mL). To this suspension, ethanol (60.0 μL) saturated with hydrogen chloride was added and the mixture was stirred at room temperature for 1 hour. The resulting crystal was collected by filtration, was washed with ethanol, and was then dried under reduced pressure to give 52.9 mg of (3R)-10-[(3S,4S)-3-cyclopropylaminomethyl-4-fluoro-1-pyrrolidinyl]-9-fluoro-3-fluoromethyl-2,3-dihydro-7-oxo-7H-pyrido[1,2,3-d.e][1,4]benzoxazine-6-carboxylic acid hydrochloride as a pale yellow crystal.

MS (FAB$^+$): m/z=438 (MH$^+$).

Elementary analysis (%): Calcd for $C_{21}H_{22}F_3N_3O_4 \cdot HCl \cdot 0.25H_2O$: C, 52.73, H, 4.95, N, 8.78; found: C, 52.68, H, 5.04, N, 8.28.

(Antibacterial Activity)

Test Example 1: In Vitro Antibacterial Activity

The in vitro antibacterial activity (as measured by the minimum inhibitory concentration (MIC)) was determined for each of the compounds of the present invention by the agar dilution method according to NCCLS (National Committee for Clinical Laboratory Standard (1997), Methods for Dilution Antibacterial Susceptibility Tests for Bacteria that grow Aerobically-Forth Edition: Approved Standard m7-A4. NCCLS, Villanova, Pa.), which involved the use of Muller-Hinton agar medium. For pneumococci and enterococci, MIC was determined by using Muller-Hinton agar medium containing 5% defibrinated equine blood. The results are shown in Table 1 below.

TABLE 1 in vitro antibacterial activity

| Strain | MIC (mg/mL) | | | | |
| --- | --- | --- | --- | --- | --- |
| | Example 1 | Example 2 | Example 4 | Example 5 | Example 6 |
| S. aureus Smith | 0.016 | 0.031 | 0.031 | 0.25 | 0.25 |
| S. aureus MR5867 | 0.016 | 0.016 | 0.031 | 0.25 | 0.25 |
| S. aureus MS16401 | 0.125 | 0.25 | 0.5 | 4 | 4 |
| S. pneumoniae Type III | 0.032 | 0.125 | 0.125 | 0.125 | 0.125 |

TABLE 1-continued

| | in vitro antibacterial activity | | | | |
|---|---|---|---|---|---|
| *E. faecalis* IID682 | 0.063 | 0.25 | 0.25 | 0.25 | 0.25 |

| | MIC (mg/mL) | | | | |
|---|---|---|---|---|---|
| Strain | Example 7 | Example 10 | Example 11 | Example 12 | Example 13 |
| *S. aureus* Smith | ≦0.008 | 0.016 | 0.008 | 0.016 | 0.008 |
| *S. aureus* MR5867 | ≦0.008 | 0.016 | 0.008 | 0.016 | 0.008 |
| *S. aureus* MS16401 | 0.063 | 0.063 | 0.031 | 0.063 | 0.031 |
| *S. pneumoniae* Type III | 0.016 | 0.031 | 0.016 | 0.063 | 0.031 |
| *E. faecalis* IID682 | 0.125 | 0.125 | 0.063 | 0.25 | 0.125 |

| | MIC (mg/mL) | | | | |
|---|---|---|---|---|---|
| Strain | Example 14 | Example 15 | Example 16 | Example 17 | Example 18 |
| *S. aureus* Smith | 0.008 | 0.031 | 0.016 | 0.008 | 0.008 |
| *S. aureus* MR5867 | 0.008 | 0.031 | 0.016 | 0.008 | 0.016 |
| *S. aureus* MS16401 | 0.031 | 0.063 | 0.063 | 0.063 | 0.063 |
| *S. pneumoniae* Type III | ≦0.008 | 0.063 | 0.032 | 0.016 | 0.016 |
| *E. faecalis* IID682 | 0.063 | 0.125 | 0.063 | 0.063 | 0.063 |

| | MIC (mg/mL) | | | |
|---|---|---|---|---|
| Strain | Example 19 | Example 20 | Example 21 | Ciprofloxacin |
| *S. aureus* Smith | 0.016 | 0.008 | 0.016 | 0.25 |
| *S. aureus* MR5867 | 0.016 | 0.016 | 0.016 | 0.25 |
| *S. aureus* MS16401 | 0.125 | 0.063 | 0.031 | 8 |
| *S. pneumoniae* Type III | 0.125 | 0.016 | 0.016 | 0.5 |
| *E. faecalis* IID682 | 0.25 | 0.063 | 0.063 | 0.5 |

*S. aureus* MR5867: methicillin-resistant *S. aureus*
*S. aureus* MS16401: quinolone-resistant *S. aureus*

INDUSTRIAL APPLICABILITY

The novel 10-(3-cyclopropylaminomethyl-1-pyrrolidinyl)pyridobenzoxazine carboxylic acid derivatives, salts and hydrates thereof, which are compounds of the present invention, are not only safe and exhibit strong antibacterial activities, but they are also effective against drug-resistant bacteria that are less susceptible to conventional antibacterial agents.

The invention claimed is:

1. A pyridobenzoxazine carboxylic acid derivative as represented by the following formula (I), or a salt or a hydrate thereof:

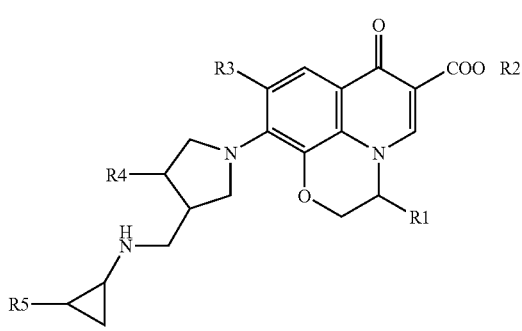

wherein R1 is a fluoromethyl group; R2 is a hydrogen atom, a lower alkyl group having 1 to 3 carbon atoms, or a pharmaceutically acceptable cation and an ester of a pro drug; R3 is a hydrogen atom or a halogen atom; R4 is a hydrogen atom, a lower alkyl group having 1 to 3 carbon atoms, a fluoromethyl group, a trifluoromethyl group or a fluorine atom; and R5 is a hydrogen atom or a fluorine atom.

2. The compound according to claim 1, a salt or a hydrate thereof, wherein in the formula (I), R3 is a fluorine atom.

3. The compound according to claim 1, a salt or a hydrate thereof, wherein in the formula (I), R3 is a fluorine atom, and R4 is a hydrogen atom, a methyl group, a fluoromethyl group or a fluorine atom.

4. The compound according to claim 1, a salt or a hydrate thereof, wherein in the formula (I), R3 is a fluorine atom, R4 is a hydrogen atom, a methyl group, a fluoromethyl group or a fluorine atom, and R5 is a hydrogen atom or a fluorine atom.

5. The compound according to claim 1, a salt or a hydrate thereof, wherein the compound of the formula (I) is (3R)-10-[(3S,4R)-3-cyclopropylaminomethyl-4-methyl-1-pyrrolidinyl]-9-fluoro-3-fluoromethyl-2,3-dihydro-7-oxo-7H-pyrido[1,2,3-d,e][1,4]benzoxazine-6-carboxylic acid, a salt or a hydrate thereof.

6. The compound according to claim 1, a salt or a hydrate thereof, wherein the compound of the formula (I) is (3R)-10-[(3S,4S)-3-cyclopropylaminomethyl-4-methyl-1-pyrrolidinyl]-9-fluoro-3-fluoromethyl-2,3-dihydro-7-oxo-7H-pyrido [1,2,3-d,e][1,4]benzoxazine-6-carboxylic acid, a salt or a hydrate thereof.

7. The compound according to claim 1, a salt or a hydrate thereof, wherein the compound of the formula (I) is (3R)-10-[(3S)-3-cyclopropylaminomethyl-1-pyrrolidinyl]-9-fluoro-3-fluoromethyl-2,3-dihydro-7-oxo-7H -pyrido[1,2,3-d,e][1,4]benzoxazine-6-carboxylic acid, a salt or a hydrate thereof.

8. The compound according to claim 1, a salt or a hydrate thereof, wherein the compound of the formula (I) is (3R)-10-[(3R)-3-cyclopropylaminomethyl-1-pyrrolidinyl]-9-fluoro-3-fluoromethyl-2,3-dihydro-7-oxo-7H -pyrido[1,2,3-d,e][1,4]benzoxazine-6-carboxylic acid, a salt or a hydrate thereof.

9. (3S)-10-[(3S,4R)-cyclopropylaminomethyl-4-fluoro-1-pyrrolidinyl]-9-fluoro-3-methyl-2,3-dihydro-7-oxo-7H-pyrido[1,2,3-d,e][1,4]benzoxazine-6-carboxylic acid, a salt or a hydrate thereof.

10. (3S)-10-[(3S,4S)-cyclopropylaminomethyl-4-fluoro-1-pyrrolidinyl]-9-fluoro-3-methyl-2,3-dihydro-7-oxo-7H-pyrido[1,2,3-d,e][1,4]benzoxazine-6-carboxylic acid, a salt or a hydrate thereof.

11. The compound according to claim 1, a salt or a hydrate thereof, wherein the compound of the formula (I) is (3R)-10-[(3S,4R) -cyclopropylaminomethyl-4-fluoro-1-pyrrolidinyl]-9-fluoro-3-fluoromethyl-2,3-dihydro-7-oxo-7H-pyrido[1,2,3-d,e][1,4]benzoxazine-6-carboxylic acid, a salt or a hydrate thereof.

12. The compound according to claim 1, a salt or a hydrate thereof, wherein the compound of the formula (I) is (3R)-10-[(3S,4S) -cyclopropylaminomethyl-4-fluoro-1-pyrrolidinyl]-9-fluoro-3-fluoromethyl-2,3-dihydro-7-oxo-7H-pyrido[1,2,3-d,e][1,4]benzoxazine-6-carboxylic acid, a salt or a hydrate thereof.

13. A pharmaceutical composition containing as an active ingredient the compound according to claim 1, a salt or a hydrate thereof, and a pharmaceutically acceptable carrier.

* * * * *